(12) United States Patent
Imori

(10) Patent No.: US 10,687,748 B2
(45) Date of Patent: Jun. 23, 2020

(54) INJECTOR

(71) Applicant: ASAHI POLYSLIDER COMPANY, LIMITED, Osaka (JP)

(72) Inventor: Hirokazu Imori, Okayama (JP)

(73) Assignee: ASAHI POLYSLIDER COMPANY, LIMITED, Osaka (JP)

( * ) Notice: Subject to any disclaimer, the term of this patent is extended or adjusted under 35 U.S.C. 154(b) by 56 days.

(21) Appl. No.: 15/678,795

(22) Filed: Aug. 16, 2017

(65) Prior Publication Data

US 2018/0360360 A1 Dec. 20, 2018

(30) Foreign Application Priority Data

Jun. 16, 2017 (JP) ................ 2017-118871

(51) Int. Cl.
*A61B 5/15* (2006.01)
*A61B 5/151* (2006.01)

(52) U.S. Cl.
CPC ...... *A61B 5/150022* (2013.01); *A61B 5/1513* (2013.01); *A61B 5/15016* (2013.01);
(Continued)

(58) Field of Classification Search
CPC ........ A61B 5/150694; A61B 5/150717; A61B 5/150725; A61B 5/15113; A61B 5/15126; A61B 5/15128; A61B 5/1213; A61B 5/15132; A61B 5/15186; A61B 5/15188; A61B 5/1519; A61B 5/150549; A61B 5/150519; A61B 5/150183; A61B 5/1411; A61B 5/15142; A61B 5/150702; A61B 5/150709; A61B 5/150022;
(Continued)

(56) References Cited

U.S. PATENT DOCUMENTS 5,385,571 A    1/1995  Morita
2001/0027327 A1* 10/2001 Schraga ........... A61B 5/150022
                                                      606/182
(Continued)

FOREIGN PATENT DOCUMENTS

CN    1512852 A    7/2004
CN    101815468 A  8/2010
(Continued)

OTHER PUBLICATIONS

Partial Search Report for corresponding European Application No. 17186353.3 dated Feb. 8, 2018.
(Continued)

*Primary Examiner* — Katherine H Schwiker
(74) *Attorney, Agent, or Firm* — Renner, Otto, Boisselle & Sklar, LLP

(57) ABSTRACT

There is provided an injector having an improvement in a linear launching profile. The injector of the present invention is used for launching a lancet to provide a pricking. The injector of the present invention comprises a plunger capable of launching the lancet in a pricking direction, an injector housing which surrounds the plunger, and an injector cap capable of being attached and detached with respect to the injector housing. In particular, an inner face of the injector cap is provided with a rib, and the rib and the plunger moving for the pricking are capable of contacting with each other.

17 Claims, 22 Drawing Sheets

(52) U.S. Cl.
CPC ........ *A61B 5/1519* (2013.01); *A61B 5/15113* (2013.01); *A61B 5/15117* (2013.01); *A61B 5/150183* (2013.01); *A61B 5/15194* (2013.01); *A61B 5/150412* (2013.01); *A61B 5/150519* (2013.01); *A61B 5/150549* (2013.01); *A61B 5/150595* (2013.01); *A61B 5/150618* (2013.01); *A61B 5/150717* (2013.01); *A61B 5/150824* (2013.01); *A61B 5/150916* (2013.01); *A61B 5/150442* (2013.01); *A61B 5/150503* (2013.01)

(58) Field of Classification Search
CPC .......... A61B 5/15003; A61B 5/150412; A61B 5/150419; A61B 5/150427; A61B 5/150435; A61B 5/151; A61B 5/15115; A61B 5/15117; A61B 5/15107; A61B 5/15109; A61B 5/15111; A61B 5/15192; A61B 5/15194; A61B 5/15196; A61B 5/15198; A61B 5/150503; A61B 5/150511; A61B 5/150175; A61B 5/150198; A61B 5/150534; A61B 5/150541; A61B 5/150557; A61B 5/150564; A61B 5/150595; A61B 5/150603; A61B 5/150625; A61B 5/150351; A61B 5/150587; A61B 5/15058; A61B 5/15; A61B 5/15019
USPC .................................................. 606/181–183
See application file for complete search history.

(56) References Cited

U.S. PATENT DOCUMENTS

| | | | |
|---|---|---|---|
| 2003/0069518 A1* | 4/2003 | Daley | A61B 5/15003 600/576 |
| 2004/0131437 A1 | 7/2004 | Kasai et al. | |
| 2006/0052809 A1 | 3/2006 | Karbowniczek et al. | |
| 2007/0055298 A1* | 3/2007 | Uehata | A61B 5/15186 606/181 |
| 2007/0083222 A1* | 4/2007 | Schraga | A61B 5/150022 606/181 |
| 2008/0319346 A1 | 12/2008 | Crawford et al. | |
| 2009/0069832 A1 | 3/2009 | Kitamura et al. | |
| 2009/0281457 A1 | 11/2009 | Faulkner et al. | |
| 2010/0249650 A1 | 9/2010 | Hikawa et al. | |
| 2011/0098735 A1 | 4/2011 | Lamps et al. | |
| 2012/0022460 A1* | 1/2012 | Horvath | A61M 5/002 604/192 |
| 2012/0191122 A1* | 7/2012 | Uchimura | A61B 5/150022 606/182 |
| 2014/0135707 A1* | 5/2014 | Suzuki | A61M 5/283 604/198 |
| 2014/0324088 A1* | 10/2014 | Chelak | A61B 5/1411 606/181 |
| 2016/0073943 A1 | 3/2016 | Cheng | |
| 2017/0021110 A1* | 1/2017 | Srinivasan | A61M 5/002 |

FOREIGN PATENT DOCUMENTS

| | | |
|---|---|---|
| CN | 101849831 A | 10/2010 |
| CN | 102014747 A | 4/2011 |
| CN | 102026580 A | 4/2011 |
| EP | 1393678 A1 | 3/2004 |
| EP | 2198781 A1 | 6/2010 |
| EP | 2263538 A2 | 12/2010 |
| WO | WO 2007/018215 A1 | 2/2007 |
| WO | WO 2008/109845 A2 | 9/2008 |
| WO | WO 2009/136171 A2 | 11/2009 |

OTHER PUBLICATIONS

Search Report for corresponding European Application No. 17186353.3 dated May 16, 2018.
Office Action for corresponding European Application No. 17186353.3 dated May 31, 2018.
Office Action for corresponding Chinese Application No. 201810606633.5 dated Nov. 19, 2019 and English machine translation.

* cited by examiner

"Twist-rotation" of cap

US 10,687,748 B2

INJECTOR

TECHNICAL FIELD

The present invention relates to an injector which is used for pricking a predetermined region of the body with a sharp tool (e.g., needle) to take a sample of a body fluid (e.g., blood). More particularly, the present invention relates to an injector used in combination with a so-called "lancet".

BACKGROUND OF THE INVENTION

In order to measure a blood sugar level of the patient with diabetes, it is required to take a sample of the blood from the patient. Various kinds of pricking devices have been proposed for sampling a small amount of the blood. The pricking device for sampling the blood is generally composed of a lancet and an injector (see Patent Document listed below). The lancet serves to actually prick the patient. While on the other hand, the injector has a function of launching the lancet toward a predetermined region (e.g., finger tip) of the patient.

Specifically, the lancet has a pricking needle, whereas the injector has a plunger equipped with a lancet-attachment portion and a spring. The spring of the plunger is used in its compressed state. The releasing of the compressed spring can give a quick movement of the plunger to launch the lancet for the pricking. For use of the pricking device, the lancet is attached to the plunger of the injector, and the compressed state of the spring is released by an actuating of a trigger of the injector. Such releasing enables the compressed spring to be expanded so that the plunger with the lancet attached thereto is launched toward the subject of the blood sampling. As a result, the predetermined region in the subject of the blood sampling is pricked by the lancet attached to the plunger.

PATENT DOCUMENTS (RELATED ART PATENT DOCUMENTS)

PATENT DOCUMENT 1: U.S. Pat. No. 5,385,571

DISCLOSURE OF THE INVENTION

Problems to be Solved by the Invention

The following pricking device has been proposed, and also been filed as a patent application (WO 2007/018215 A1, filed date: 8 Aug. 2006, title of the invention: "PRICKING DEVICE, AS WELL AS LANCET ASSEMBLY AND INJECTOR ASSEMBLY THAT CONSTITUTE THE PRICKING DEVICE"). Referring to the accompanying drawings, the proposed pricking device, which is composed of a lancet assembly and an injector assembly, will be briefly explained below (note that the term "injector assembly" will be hereinafter referred to also as "injector"). FIG. 16 shows an external appearance of a lancet assembly 100', and FIG. 17 shows an external appearance of an injector 200'. As shown in FIG. 16, the lancet assembly 100' is composed of a lancet 101' and a protective cover 102'. As shown in FIGS. 18 and 19, the lancet 101' is composed of a lancet body 104', lancet cap 106' and a pricking needle 105'. The pricking needle 105' is situated in both of the lancet body 104' and the lancet cap 106', pricking needle 105' being made of metal, the lancet body 104' and the lancet cap 106' being made of resin. The tip of the pricking needle 105' is covered with the lancet cap 106'. The lancet cap 106' and the lancet body 104' are integrally connected together by a weakened part 108'. As shown in FIGS. 16 and 19, the protective cover 102' is provided to enclose a part of the lancet body 104'. Such lancet 100' is loaded into the injector 200', and thereafter the lancet cap 106' is removed. By the removal of the lancet cap, the tip of the pricking needle 105' is exposed, and thereby the lancet becomes ready for pricking.

The injector 200' shown in FIG. 17 can be used in combination with the lancet 100' to launch the lancet body with the tip of the pricking needle 105' being exposed. The injector 200' comprises a plunger 204'. The plunger 204' is capable of engaging with a rear end portion of the lancet body to launch the lancet body in the pricking direction (see FIG. 20). As shown in FIG. 20, the lancet 100' is loaded into the injector 200' by inserting the lancet 100' into the injector 200' through a front end opening 214' of the injector 200'. As shown in FIG. 21, when the lancet has been inserted to some degree, a rear portion 116' of the lancet 100' is held by tips 264' and 266' of the plunger 204'. Subsequently, when the insertion of the lancet is continued, the plunger 204' is thrust backward so that the launching energy is stored. That is, the plunger 204' is forced to move backward (i.e., the plunger is forced to retract), which can compress a spring (not shown) provided in the plunger 204'. This means that, when the compression of the spring is released, the plunger instantly moves forward to launch the lancet. FIG. 22 shows the injector 200' in the state where the plunger has retracted and the launching energy has been stored therein.

After the loading (i.e., attaching) of the lancet 100' into the injector 200' is completed, the lancet cap 106' is removed to expose the tip of the pricking needle 105'. The removal of the lancet cap 106' will be described as follows:

As shown in FIGS. 18 and 19, the lancet body 104' and the lancet cap 106' are in an integral connecting with each other by the weakened part 108' disposed between the lancet body 104' and the lancet cap 106'. The weakened part 108' is broken by rotating the lancet body 104' and the lancet cap 106' around the pricking needle in the reverse direction to each other (see FIG. 22 in which the rotation of the lancet cap in the direction "G" is shown), whereby the removal of the lancet cap 106' can be performed. Namely, the tip of the pricking needle 105' is exposed by so-called "twist off".

In order to conduct the pricking operation, the front end opening 214' of the injector 200' is applied to a predetermined region to be pricked (for example, a finger tip). Subsequently, the press part 542' of a trigger component 514' is pushed. See FIG. 23. The pushing of the press part 542' results in an instantaneous expansion of the compressed spring, and thereby forcing the plunger 204' to move forward to prick the predetermined region by the pricking needle of the lancet.

With respect to the above-described pricking device, the inventor of the present application has found that the injector, which serves to launch the lancet, still has room for the following improvements.

In order to reduce the pain felt by the subject of the blood sampling at the time of the pricking, a needle of the lancet is processed to have an extra fine tip. And also, a measure is often taken to prevent the needle tip from bending when the lancet is used. In particular, a linearity of the plunger of the injector when being moving for launching the lancet can effectively contribute to a reduction in the pain. This means that, even in the case of the extra fine tip of the lancet and no bending of the lancet tip, an insufficient linearity of the moving plunger can cause an increase in the pain at the time of the pricking, the plunger having the lancet attached thereto.

In order to attach the lancet to the injector, a cap of the injector (which will be hereinafter referred to also as "injector cap") is detached from the injector so that the lancet is attached to the plunger of the injector. The detached cap is subsequently returned to the original position of the injector (i.e., the detached cap is re-attached to the injector) after the attaching of the lancet to the plunger. Such handling of the injector cap is necessary for the pricking operation. Thus, a simpler handling of the injector cap can bring about more convenient for user. Further, at a point in time after the detached cap is re-attached to the injector, an incidental or unintentional detaching of the cap should be avoided in terms of safety of the injector.

The present invention has been devised to address the matters as described above. As such, an object of the present invention is to provide a more suitable injector in terms of the linearity of the plunger and/or the convenience/safety of the injector cap.

Means for Solving the Problems

In order to achieve the above object, the present invention provides an injector for launching a lancet to provide a pricking, the injector comprising:
 a plunger capable of launching the lancet in a pricking direction, the lancet being in attachment to the plunger;
 an injector housing which surrounds the plunger; and
 an injector cap capable of being attached and detached with respect to the injector housing,
 wherein an inner face of the injector cap is provided with a rib, and
 wherein the rib of the injector cap and the plunger of the injector housing are capable of contacting with each other at a point in time after a launching of the plunger for the launching of the lancet.

One of the characterizing features of the injector according to the present invention, which will be hereinafter referred to also as "FIRST FEATURE", is that the rib provided at the inner face of the injector cap and the plunger moving for the launching of the lancet are capable of contacting with each other. At a point in time of the pricking, a front end portion of the plunger temporarily becomes positioned inside the injector cap, and thus the inner rib of the injector cap and the outer surface of the plunger make contact with each other.

In order to achieve the above object, the present invention also provides an injector for launching a lancet to provide a pricking, the injector comprising:
 a plunger capable of launching the lancet in a pricking direction, the lancet being in attachment to the plunger;
 an injector housing which surrounds the plunger; and
 an injector cap capable of being attached and detached with respect to the injector housing,
 wherein the injector cap has a first raised portion at an inner face of the cap, and
 wherein the injector housing has a pair of banks in an outer face of the housing, and also a second raised portion at a groove region provided inside the banks.

One of the characterizing features of the injector according to the present invention, which will be hereinafter referred to also as "SECOND FEATURE", is that the inner face of the injector cap has the first raised portion, whereas the outer face of the housing has the pair of banks and the second raised portion inside the banks. More specifically, the injector cap is attachable to the injector housing, and also the cap is detachable from the housing, wherein the first raised portion is provided in the cap, whereas the banks and the second raised portions positioned at a groove region inside the banks are provided in the housing.

Effect of the Invention

The injector according to "FIRST FEATURE" of the present invention has an improved linearity of launching. This makes it possible to reduce the pain felt by the subject of the blood sampling at the time of the pricking. More specifically, the rib provided at the inner face of the injector cap and the plunger moving for launching the lancet are capable of contacting with each other, and thereby the linearity of the plunger is improved at the time of pricking. The improved linearity of the plunger means an improvement in the linearity of needle of the lancet attached to the plunger. In particular, the injector according to the present invention can give a correction of a pricking pathway of the plunger at a particular point which is closer to the pricking point of the subject of the blood sampling. This can more effectively reduce the pain felt by the subject of the blood sampling at the time of the pricking.

The injector according to "SECOND FEATURE" of the present invention has an increased convenience and/or an improved safety at a point in time when the injector is operated by the user. Specifically, the inner face of the injector cap has the first raised portion, whereas the outer face of the housing has the banks and also the second raised portion inside the banks, and thereby making it possible to perform a more suitable "snap fitting" at the time of the attaching of the cap. More specifically, when the injector cap is attempted to be attached to the injector housing, the cap can be loaded straightforwardly/in non-slant state toward the injector housing so that the suitable snap fitting is achieved, which leads to a completed attaching of the cap. Once the injector cap is attached, the cap cannot be detached from the injector housing straightforwardly. This means that the incidental or unintentional detachment of the cap is prevented so that a more suitable safety is ensured in the injector. While on the other hand, when the injector cap is twist-rotated about the axis of the injector with respect to the injector housing, the snap fitting can be released. This makes it possible for the attached cap to be easily detached when the cap detachment is attempted for the operating of the injector. In particular, the twist direction of the cap is not limited to one direction. The injector cap thus has a reversible direction of the twist, i.e., reversible direction of cap rotation for the attaching and detaching of the cap.

BRIEF DESCRIPTION OF THE DRAWINGS

FIG. 1A shows the state where the injector cap is in attachment to the injector housing, whereas FIG. 1B shows the state where the injector cap has been detached from the injector housing.

MODES FOR CARRYING OUT THE INVENTION

With reference to the accompanying drawings, an injector of the present invention will be described. The components/parts/portion in drawings are schematically illustrated for a better understanding of the invention.

Figure 1A:
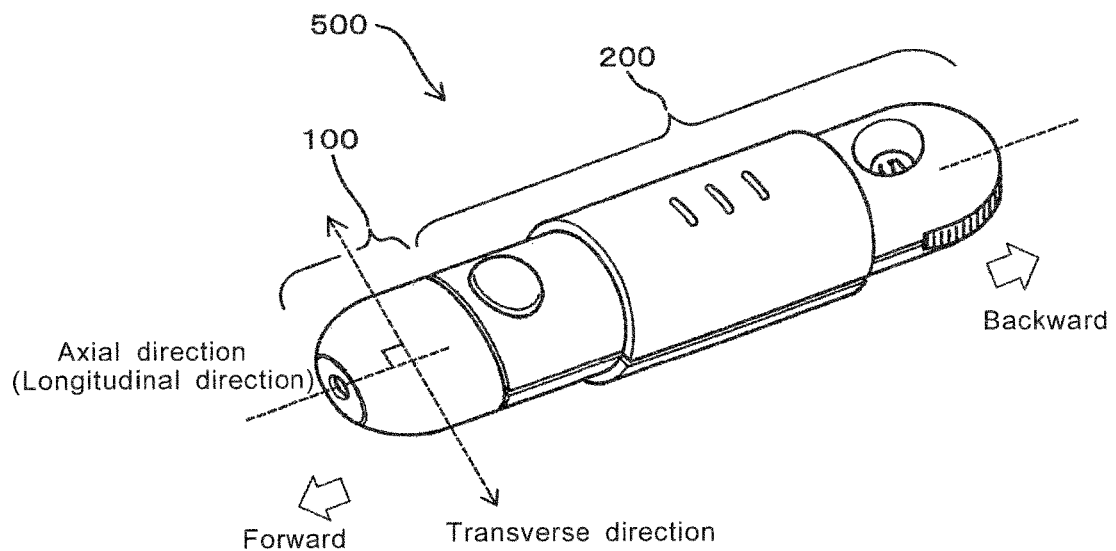
FIGS. 1A and 1B show perspective views illustrating an appearance of an injector according to an embodiment of the present invention. In particular.

The term "direction" as used herein is defined as follows: The direction in which the plunger of the injector moves for launching the lancet is regarded as a "forward" direction, and the reverse direction thereto is regarded as a "rearward"/"backward" direction. The direction orthogonal to the axis of the injector or orthogonal to the longitudinal direction of the injector is regarded as a "transverse direction". Furthermore, the term "axis" regarding the injector refers to a longitudinal axis of the injector (i.e., the axis along the longitudinal direction of the injector), and thus it can correspond to the pricking direction. These terms concerning the directions are shown in the drawings (FIG. 1A in particular).

The present invention relates to an injector. The basic structure of the injector as well as the use embodiment of the injector will be described, followed by the detailed explanation for the characterizing features of the injector according to the present.

(Basic Structure and Use Embodiment of Injector)

The injector to which the present invention is directed is a device having a launching function. Thus, the injector of the present invention is a launching device. More specifically, the injector of the present invention is used in combination with a so-called "lancet", and has a function of launching the lancet to provide a pricking, the lancet being in attachment to the injector. That is, the use of the injector makes it possible to launch the lancet having a pricking needle toward a region to be pricked.

Figure 1B:
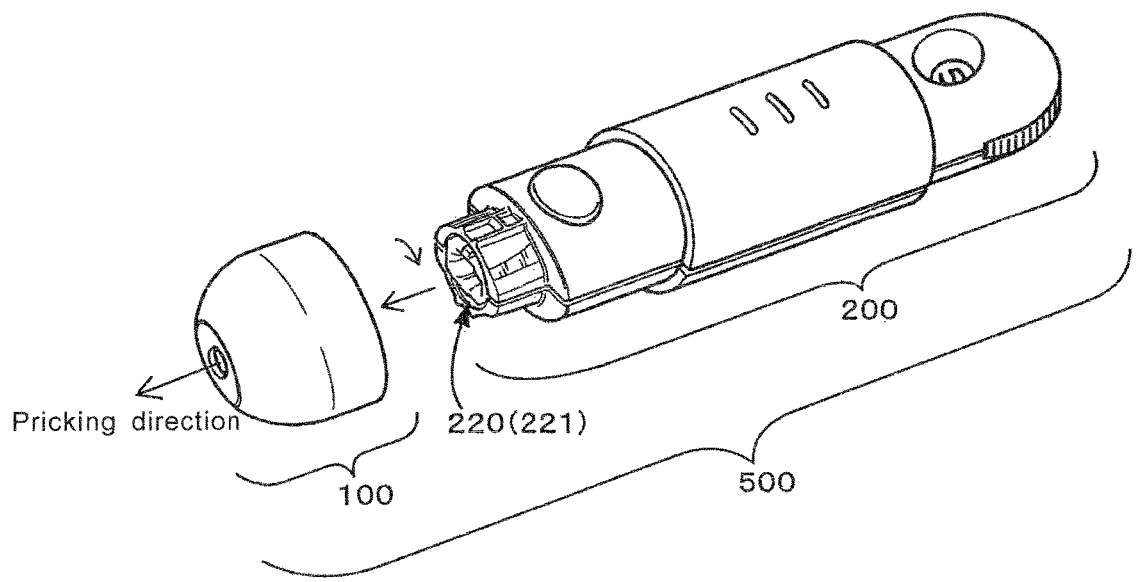
Figure 2A:
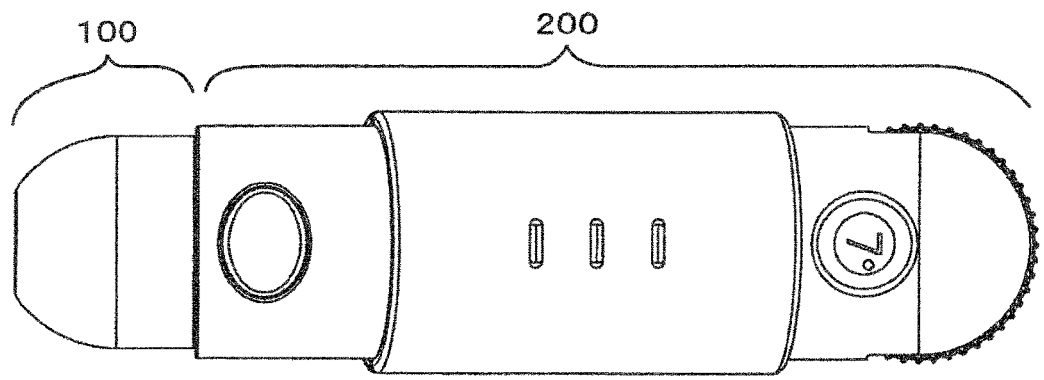
FIGS. 2A to 2C are schematic plan and cross-sectional views illustrating the injector according to an embodiment of the present invention (FIG. 2A: plan view, FIG. 2B: cross-sectional view, FIG. 2C: another cross-sectional view).
Figure 2B:
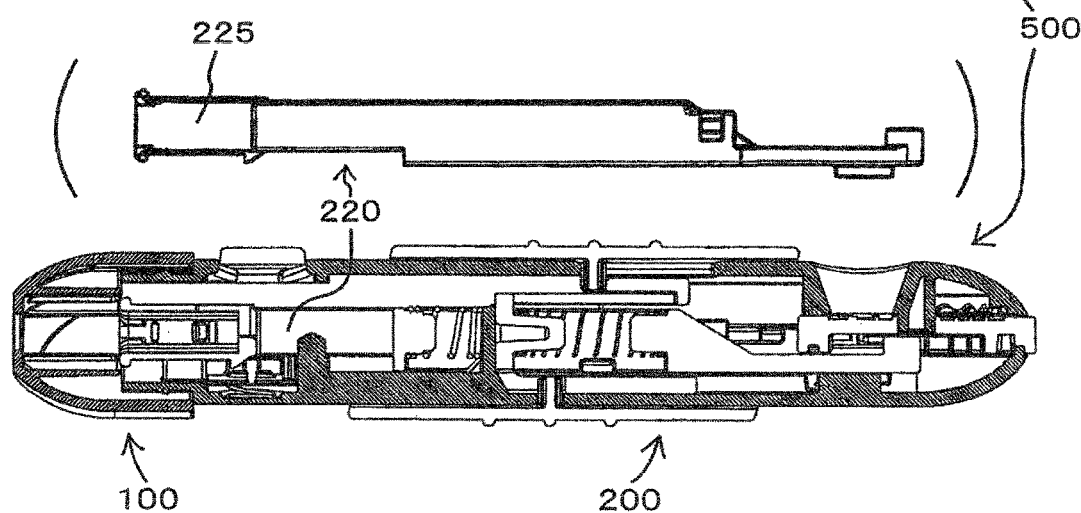
Figure 2C:
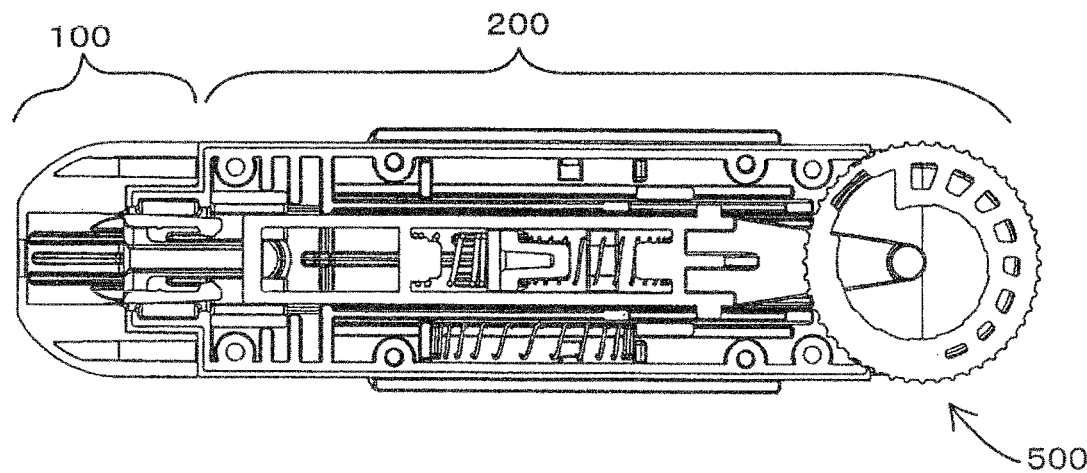

FIGS. 1A and 1B show an appearance of the injector 500. FIGS. 2A to 2C show not only the appearance of the injector 500, but also the internal structure thereof. The injector comprises an injector housing and an injector cap as outer structures of the injector. As shown in FIGS. 1A-1B and 2A-2C, the injector 500 at least comprises the injector cap 100 located forward with respect to the injector housing, and also the injector housing 200 located rearward with respect to the injector cap.

In the interior of the injector housing 200, a plunger 220 is provided, as shown in FIG. 2. The plunger has a lancet holder 225 at the front end thereof. The lancet holder 225 is used for the attaching of the lancet to the injector. The plunger also has a suitable spring for providing a launching force with the plunger (to which the lancet is attached) in use of the injector. The injector housing 200 surrounds the plunger 220 to which the lancet is attached, and thus the plunger within the injector housing can launch the lancet attached thereto in the pricking direction.

The injector cap 100 is attachable to the injector housing 200, and also the injector cap 200 is detachable from the injector housing 200. At a point in time before the use of the injector, i.e., at the time of non-use of the injector, the injector cap 100 is usually in attachment to the injector housing 200. When the injector is meant to be used, the injector cap 100 is detached from the injector housing 200 (see FIG. 1B). The detachment of the injector cap 100 enables the front end portion 221 of the plunger 220 positioned inside the injector to be exposed so that the lancet can be attached to the plunger 220. After the attaching of the lancet to the plunger, the cap is returned to the original position of the injector housing. That is, the injector cap, which has been once detached, is re-attached to the injector housing 200 to perform a subsequent pricking operation.

Figure 3A:
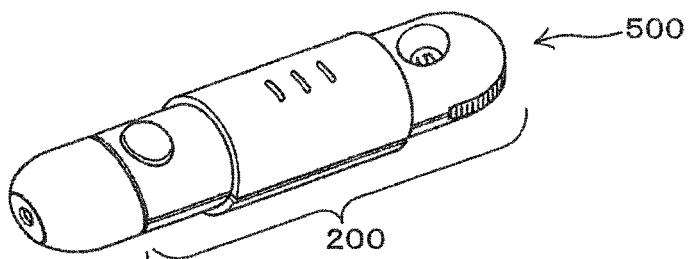
FIGS. 3A to 3F are schematic perspective views illustrating the exemplified changes in the injector over time during the using thereof.
Figure 3B:
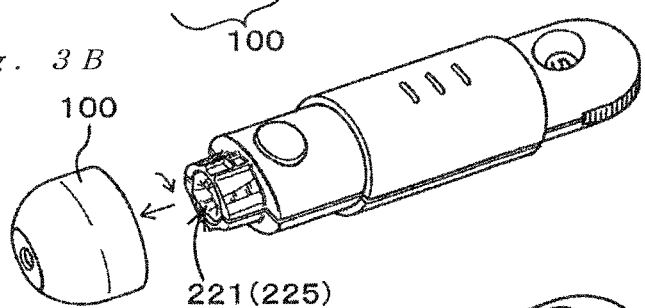
Figure 3C:
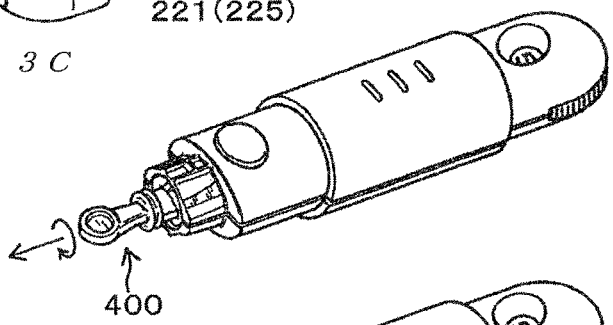

FIGS. 3A to 3F show the exemplified changes in the injector over time during the using thereof. The first thing to do for the use of the injector 500 is to detach/remove the injector cap 100 from the injector 500, as shown in FIGS. 3A and 3B. Subsequently, as shown in FIG. 3C, the lancet 400 is attached to the front end portion 221 of the plunger. That is, the lancet is attached to the lancet holder 225 of the plunger so that the lancet 400 is loaded to the injector 500.

Figure 3D:
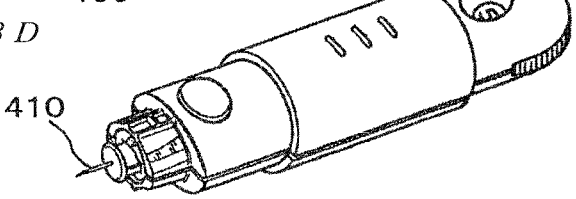
Figure 3E:
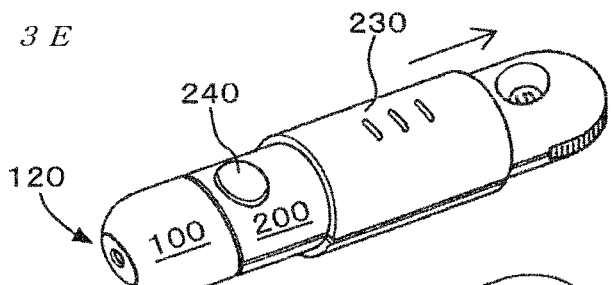

Subsequent to the attaching of the lancet 400, a cap of the lancet 400 is twisted to be removed from the lancet, and thereby enabling a pricking needle 410 of the lancet to be exposed (see FIGS. 3C and 3D). Subsequently, the injector cap 100 is returned to the original position of the injector, as shown in FIG. 3E. In other words, the injector cap 100 which has been once detached from the injector, is re-attached to the injector housing 200. Next, a charge part 230 of the injector is push back so that the charge part slides rearward on the body of the injector. This makes it possible to compress a fire spring (not shown) which cooperates with the charge part 230, and thereby a force necessary for launching the lancet is stored in the plunger. The fire spring and the plunger are in connection with each other in the injector. Thus, the compressed state of the fire spring is kept by an engagement of the plunger with the internal structure of the injector housing. As a result, the injector becomes ready for "fire", i.e., ready for pricking.

Figure 3F:
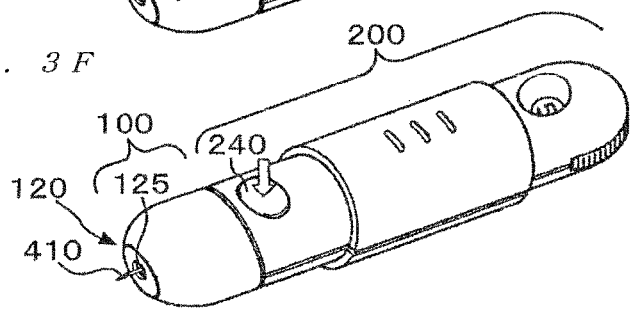

For carrying out the pricking operation, the front end of the injector (i.e., an injector portion designated by the reference numeral "120" in FIG. 3E) is applied to a predetermined region to be pricked (for example, the predetermined region being a finger tip). Subsequently, a launch button 240 of the injector is pushed. The pushing of the launch button 240 results in an instantaneous expansion of the compressed spring, and thereby forcing the plunger to be launched forward. Thus, a lancet body equipped with the pricking needle, which is in attachment to the plunger, is also forced to be launched forward for performing the pricking, i.e., launched in the pricking direction. FIG. 3F shows the injector at the time of the pricking caused by the pushing of the launch button 240. In FIG. 3F, the pricking needle 410 is exposed from the front end 120 (more specifically, the needle is exposed from a front opening 125 of the injector cap 100). After the launching of the plunger, followed by the pricking, the plunger is forced to be moved backward such that it retracts toward the injector housing by the action of a return spring (not shown) provided inside the injector housing 200.

At a point in time after the pricking, the injector cap 100 is re-detached from the injector so that the used lancet is removed from the plunger. As such, the injector for launching the plunger (i.e., injector for launching the lancet) according to the present invention is suitable for use with a so-called disposable lancet.

Characterizing Features of Injector of Present Invention

The injector of the present invention has characterizing features associated with the injector cap, in particular. One of the features is concerned with "linearity of pricking needle". The other is concerned with "convenience/safety of injector cap".

(Linearity of Needle Pricking)

Figure 4:
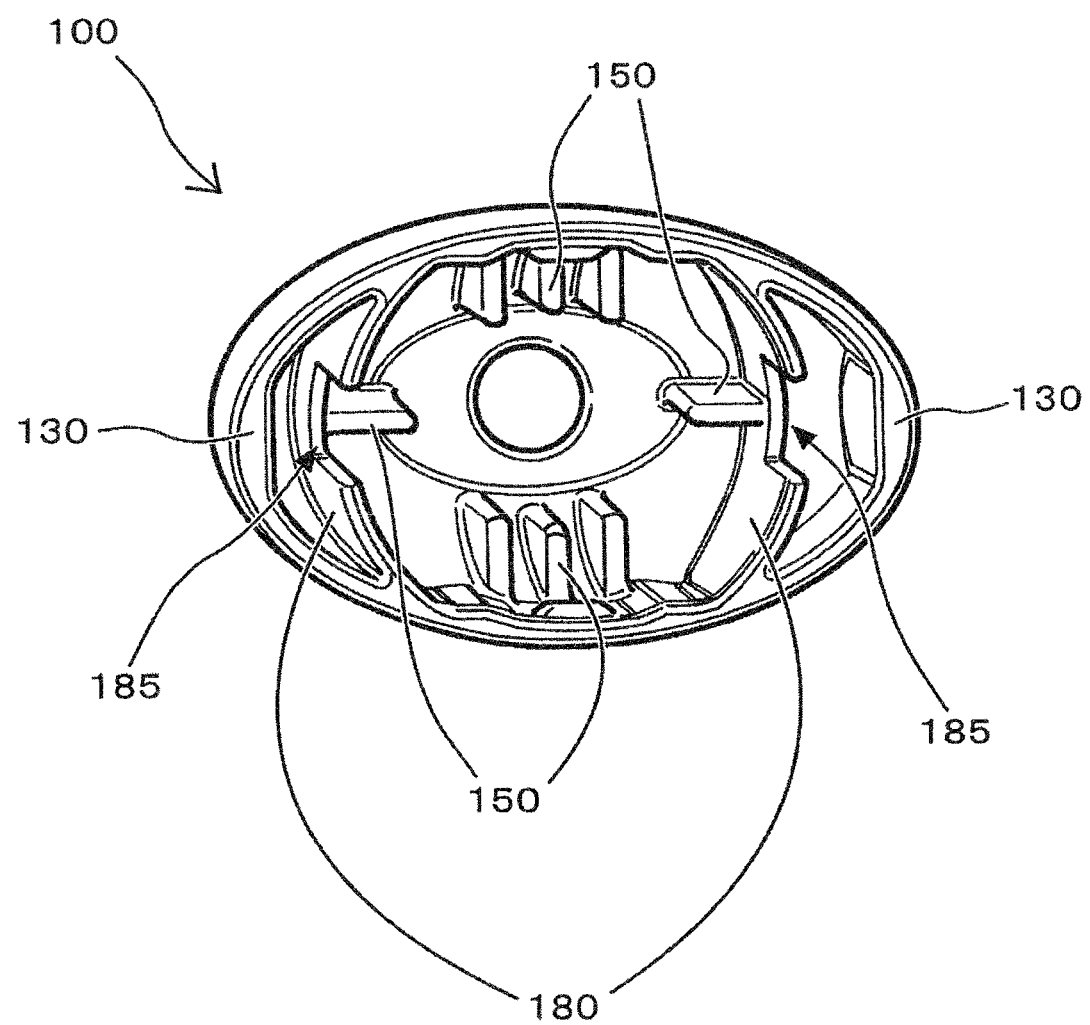
FIG. 4 is a schematic perspective view of an injector cap wherein the inner side of the cap is shown.

The injector with the feature of "linearity of pricking needle" has a rib 150 in the inner face of the injector cap 100, as shown in FIG. 4. Because of "inner face", the rib 150 corresponds to an internal structure of the injector, especially the internal structure of the injector cap 100. Since the rib 150 is provided in the injector cap 100, the rib according to the present invention can be positioned closer to the region to be pricked (i.e., the rib according to the present invention is positioned much closer to the region to be pricked in the subject of the blood sampling, especially compared to a case where a rib is provided with the injector housing).

Figure 5:
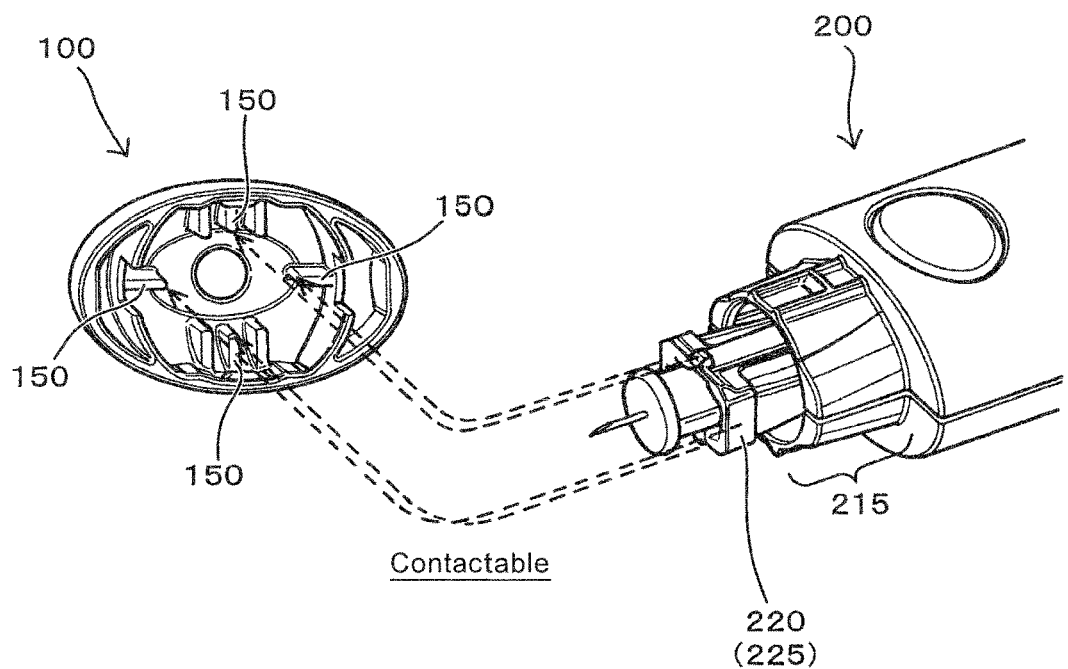
FIG. 5 is a schematic perspective view for explaining a contacting between a rib and a plunger at the time of pricking.
Figure 6:
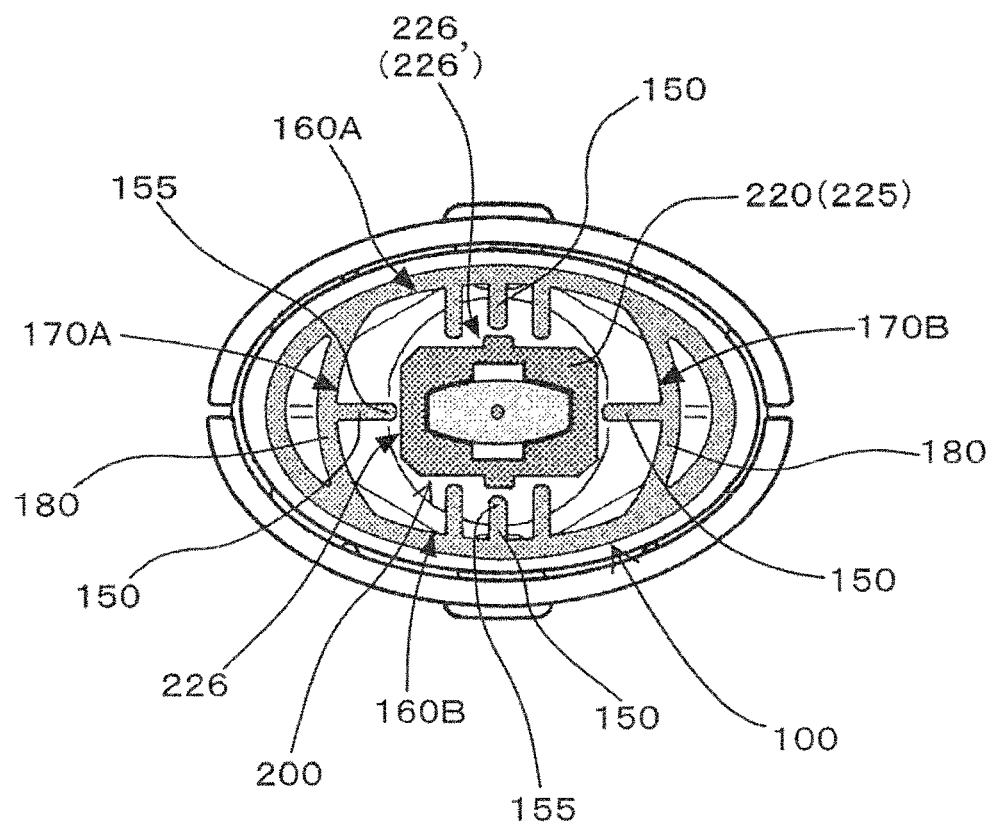
FIG. 6 is a schematic cross-sectional view for explaining a capability for a contacting between a rib and a plunger at the time of pricking.

As shown in FIGS. 5 and 6, the rib 150 of the injector cap can cooperate with a part/portion provided in the injector housing 200 at the time of pricking. Specifically, "the plunger 220 which has been launched" and "the rib 150" are capable of contacting with each other. During the time of the pricking, the injector cap 100 is in attachment to the injector housing 200 (see FIG. 3E). In the course of the pricking, "the rib 150" and "the launched plunger 220 moving in the pricking direction and also in the opposite direction thereto" make contact with each other. That is, the rib 150 of the injector cap 100 and the plunger 220 provided inside the injector housing 200 are capable of contacting with each other, the plunger being moving for the launching for the launching of the lancet. In particular, the lancet holder 225 provided at the front end of the plunger is capable of contacting with the rib 150.

The phrase "capable of contacting" as used herein means an embodiment of the injector in a broader sense wherein the plunger which has been launched for pricking can make contact with the rib. In a narrower sense, such phrase means an embodiment of the injector wherein the moving plunger (especially, the moving "lancet holder" provided in the front end thereof) caused by the pushing of the launch button can make contact with the rib of the injector cap.

In a preferred embodiment of the invention, the plunger and the rib are capable of contacting with each other during the pricking process in which the launched plunger moves forward in the pricking direction, and subsequently it moves backward in the opposite direction thereto to retract toward the injector housing. It should be noted that, according to a preferred embodiment of the present invention, a constant contact between the plunger and the rib is not necessarily required during all the forward and backward movements of the launched plunger.

The injector of the present invention has an improved linearity of "launch" due to the contact between the rib at the side of the injector cap and the plunger at the side of injector housing. Specifically, the improvement in the linearity in terms of the pathway of the plunger at the time of pricking leads to the improved linearity on the pricking needle of the lancet attached to the plunger. In particular, what is a significant part serving to improve the linearity is the rib provided in the injector cap to be directly applied to the subject of the blood sampling, which means that the pricking pathway of the plunger according to the present invention can be corrected at a point closer to the pricking point of the subject of the blood sampling. The correction of the pricking pathway of the plunger at the particular point closer to the pricking point can more effectively improve the linearity of the pricking needle, which can more effectively reduce the pain felt by the person to be pricked (i.e., the subject of the blood sampling) at the time of the pricking. While not wishing to be bound by any theory, the reduced pain is believed to be attributable to a more effective reduction of "adverse phenomenon of hollowing or scratching the pricked portion by the moving needle", the reduction being due to a suppression of the wobbling, jiggling or undulating of the pricking needle at the particular point closer to the pricking point at the time of pricking. Further, the injector of the present invention can ensure a constant pathway of the needle even if the various users operate the injector. Even when the different users operate the injector, substantially the constant pathway of the pricking needle can be given. This can bring about an advantageous effect in that variation from user to user can be significantly reduced.

It is preferred that the rib 150 of the injector cap 100 is capable of making contact with the front portion of the plunger 220 (i.e., forward portion of the plunger). The contacting between the rib and the front portion of the plunger can more particularly contribute to a prevention of the wobbling, jiggling or undulating of the pricking needle, which can more effectively reduce the pain at the time of pricking. In this regard, the lancet 400 is attached to the lancet holder 225 of the plunger 220 in use of the injector, in which case the lancet holder 225 is preferably capable of making contact with the rib 150 of the injector cap 100 (see FIG. 6). It is particularly preferred that the outer face 226 of the lancet holder 225 (to which the lancet 400 is attached) is capable of making contact with the top edge/apex 155 of rib 150. As shown in FIG. 6 by the reference numeral 226', the outer surface of the lancet holder may have a convex form for a suitable contact between the lancet holder and the rib. For example, the outer surface of the lancet holder may be provided with a raised portion which extends along the pricking direction.

The skilled persons' recognition regarding the injector of the prior art will be now described. In the prior art, there was a preconception that a rib for improving the linearity cannot or should not be provided in the injector cap. The reason for this was that a lancet holder was designed to expand outward in the radial direction thereof upon attaching the lancet into the holder, the outward expansion being due to the presence of a slit of the holder. In most cases, the lancet holder according to the prior art has the slit in the body of the holder to provide its increased versatility wherein any of the lancets with somewhat different sizes from each other can be attached into the holder. If a rib for the improved linearity were provided in the injector cap, there would be a concern for the skilled persons that the launched holder could collide against the rib due to the outward expansion of the holder, and thereby inhibiting the desired pricking. This means that the skilled persons in the prior art had their recognitions that the pricking needle could not protrude from the pricking opening of the injector in the case of the rib provided in the injector cap. As a result of the present inventor's extensive studies about the injector, it has been found that, even if the rib is provided in the injector cap, the improved linearity can be achieved with no undesirable collision of the launched holder against the rib. In this regard, the injector of the present invention intentionally has no slit in the lancet holder of the plunger (i.e., no slit configured to expand upon attaching the lancet into the holder) to avoid the collision of the holder with the rib. Accordingly, the lancet holder provided in the injector according to the preferred embodiment of the present invention can be also referred to "non-slit type holder" with no expansion-slit in the body thereof.

In a preferred embodiment, the rib is provided as a pair of ribs. For example in the cross-sectional view of FIG. 6, the opposed faces of the injector cap have the pair of ribs 150. More specifically, each of the opposed inner faces 160A and 160B is provided with the rib 150 to form the pair of ribs. As for the cross-sectional view of FIG. 6, each of the opposed inner faces 170A and 170B is also provided with the rib 150 to form another pair of ribs.

The phrase "provided as a pair of ribs" regarding the injector cap means in a broader sense that one of ribs is arranged in an opposed relationship with respect to the other of ribs. In a narrower sense, such phrase means that one of ribs is arranged in an opposed relationship with respect to the other of ribs such that the lancet holder of the plunger which has been launched becomes positioned between them when the injector is used.

The opposed arrangement of the paired ribs can more effectively reduce an undesirable deviation in the correction of the pricking pathway of the launched plunger, which leads to a more effectiveness in the improved linearity.

More preferably, the two pairs of ribs are provided wherein an opposing direction of the ribs in one of the two pairs is orthogonal to another opposing direction of the ribs in the other of the two pairs. For example, as shown in FIG. 6, the pair of ribs 150 provided in the opposed inner faces 160A and 160B of the cap may be located in the orientation orthogonal to the another pair of ribs 150 provided in the opposed inner faces 170A and 170B of the cap. The orthogonality of the two pair makes it possible to effectively reduce the undesirable deviation in both "left-right direction" (e.g., horizontal direction) and "upper-lower direction" (e.g., vertical direction) in the cross-sectional view of FIG. 6, which leads to a more efficient improvement in the linearity of the pricking needle.

The number of the rib provided in the injector cap is not limited to one, but may be plural. In other words, the rib may be provided as plural ones. In terms of "pair of ribs" (i.e., paired ribs), it is preferred that even number of ribs are provided. The plurality of ribs may be symmetrical to each other in the cross-sectional view of the injector cap, the view being taken along a direction orthogonal to the pricking direction. See FIG. 6, for example. More specifically, the plurality of ribs may be point-symmetrical or line-symmetrical to each other in the cross-sectional view of the injector cap. The term "symmetrical" as used herein means that one of ribs has a point-symmetric or line-symmetric relationship with the other of ribs in the cross-sectional view of the injector cap, the view being taken along the transverse direction of the injector. In other words, if one of ribs is rotated about the center of symmetry by 180 degree, it can be overlapped with the other of ribs, and vice versa. Alternatively, if one of ribs is folded at the axis of symmetry, it can be overlapped with the other of ribs, and vice versa. These symmetric arrangements of the ribs can promote a reduction in the undesirable deviation in the correction of the pricking pathway of the launched plunger.

In a preferred embodiment, the rib protrudes in approximately the perpendicular direction with respect to the inner surface/internal surface of the injector cap. As shown in FIG. 6 for example, the ribs 150 protrude in approximately the perpendicular direction with respect to the inner surface 160A and/or the inner surface 160B of the injector cap. In a case where the inner surface is a curved surface, the rib may protrude in approximately the normal direction at such a rib provision point of the surface that the rib is directly provided, as can be appreciated from the embodiment of the injector cap of FIG. 6. The phrase "approximately the perpendicular" as used herein means that it is not necessarily an exact one, but may be somewhat different from the exact one wherein the rib protrudes in the direction forming an angle of 0° to 10° with respect to the normal line at the rib provision point of the surface.

The rib 150 protruding in approximately the perpendicular direction facilitates the launched plunger to more suitably make contact with the top edge 155 of the rib 150, and thereby avoiding an excessive friction resistance of the plunger, the friction resistance being come from the rib. This can achieve the improved linearity with no excessive loss of the launching force for the plunger.

The protruding size of the rib (in particular, the height dimension of the rib) is not particularly limited as long as it can contribute to the contact between the rib and the plunger. By way of example, the rib may have its protruding height such that a slight clearance is formed between the top edge of the rib and the outer face of the hypothetical plunger (i.e., the plunger which is hypothetical to have moved forward with no wobbling, jiggling or undulating thereof) in the cross-sectional view of FIG. 6. Such small clearance may be within about 1 mm, for example within 0.8 mm or within 0.5 mm.

As shown in FIGS. 4 to 6, the injector cap 100 with the rib 150 formed therein may have a flattened shape as a whole appearance thereof. For example, the injector cap may have approximately an elliptical shape in a cross-sectional view of the cap, the view being taken along a direction orthogonal to the pricking direction. In other words, the cross-sectional view of the injector cap 100 as shown in FIG. 6 has approximately the elliptical or oval shape/form as a whole.

The phrase "approximately an elliptical shape" as used herein means that it is not limited to an exact elliptical shape, but it includes any shapes which the skilled persons would usually regard as "elliptical shape" in general. Thus, a curving contour of the elliptical injector cap may be any one as long as the cross-sectional form of the injector cap has a short axis and a long axis both of which are orthogonal to each other.

Approximately the elliptical shape of the injector cap can provide a large degree of design freedom on the number of the rib, for example. As shown in FIG. 6, approximately the elliptical shape of the injector cap can facilitate achieving such a particular design that the number of ribs 150 at the opposed inner faces 160A and 160B is different from the number of ribs 150 at the opposed inner faces 170A and 170B. Such difference in the number of the ribs leads to a suitable arrangement of the rib to conform to the form of the lancet holder (e.g., cross-sectional shape of the lancet holder).

As shown in FIG. 6, the injector cap further comprises a pair of curved walls 180 which are arranged inside an internal face of the cap wall. In the case where the injector cap has approximately the elliptical shape in the cross-sectional view thereof, the curved walls may extend along the short axis of the approximately the elliptical shape in the cross-sectional view. In this case, the rib 150 capable of contacting the plunger 220 (e.g., the lancet holder 225 thereof) may be provided at the inner face of the curved walls 180.

(Convenience/Safety of Cap)

The injector with the feature "convenience/safety of cap" has a unique component/part/portion associated with the attaching and detaching of the injector cap.

Figure 7:
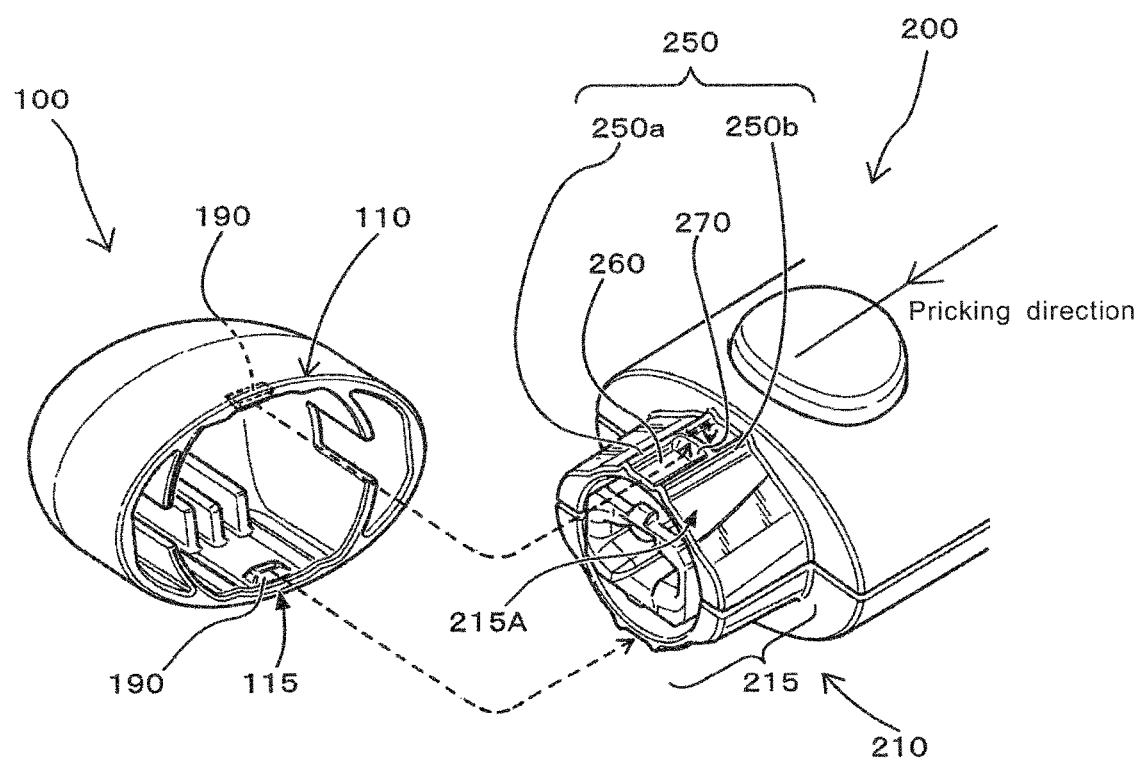
FIG. 7 is a schematic perspective view of an injector cap and an injector housing, the view being for explaining the feature "convenience/safety of cap".

According to the injector with the above feature, the injector cap 100 has a first raised portion 190 at an inner face (e.g., inner surface) of the cap, as shown in FIG. 7. As can be seen from FIG. 7, the first raised portion 190 has a locally raised form of the inner surface of the injector cap. While on the other hand, the injector housing 200 has a pair of banks 250 (250a, 250b) in an outer face (e.g., outer surface) of the housing, and also a second raised portion 270 at a groove region 260 provided inside the banks. As for the groove region of the injector housing, it is located between one (i.e., bank 250a) of the paired banks and the other (i.e., bank 250b) of the paired banks. Similar to the first raised portion 190, the second raised portion 270 has a locally raised form of the outer surface of the injector housing 200.

It is preferred that the first raised portion 190 is positioned adjacent to a rear edge 110 of the injector cap 100, as shown in FIG. 7. More preferably, the first raised portion 190 is positioned immediately adjacent to the rear edge 110. In other words, the first raised portion 190, which is located relatively rearward in the injector cap 100, is preferably positioned closer to the rear edge 115 of the injector cap 100. While on the other hand, it is preferred that the second raised portion 270 is positioned at a forward portion 210 (e.g., forward edge portion) of the injector housing 200 and on the outer surface of the housing 200. More preferably, the second raised portion 270 is positioned at a local region of the outer surface of the injector housing 200, the local region being to be overlapped with the attached injector cap 100.

In particular, the second raised portion 270 is positioned at the inside region of the pairs of banks 250, i.e., at the groove region 260. It is preferred that each of the banks 250 extends along the pricking direction. As shown in FIG. 7, one bank 250a of the pair is opposed to the other bank 250b of the pair such that they extend along the axis direction of the injector. The second raised portion 270 is preferably located such that it lies between one bank 250a and the other bank 250b. Such extending of the banks enables the first raised portion 190 to suitably cooperate with the banks 250 (i.e., the groove region inside the banks) upon the attaching and detaching of the injector cap. The second raised portion 270 may have a continuous form with at least one of the paired banks 250. This means that the second raised portion 270 and the banks 250 may have an integrated form with each other. In this regard, the second raised portion 270 may have a bride form between one bank 250a and the other bank 250b of the paired banks.

In the injector of the present invention, the first raised portion is capable of fitting to the groove region. In particular, when the injector cap 100 is attached to the injector housing 200, the first raised portion 190 of the injector cap 100 can be fitted to the groove region 260 of the injector housing 200. The width dimension of the first raised portion 190 may be approximately the same as the width dimension of the groove region 260. As such, the first raised portion 190 of the injector cap 100 can be suitably fitted into the paired banks 250 such that the first raised portion 190 becomes positioned between one bank 250a and the other bank 250b of the pair. Such fitting enables the first raised portion 190 of the injector cap 100 to be guided along the groove region 260 of the injector housing, and thereby facilitate a suitable attaching of the injector cap. In particular, the injector cap can be attached straightforwardly/in non-slant state to the injector housing along the axis of the injector.

Figure 8A:
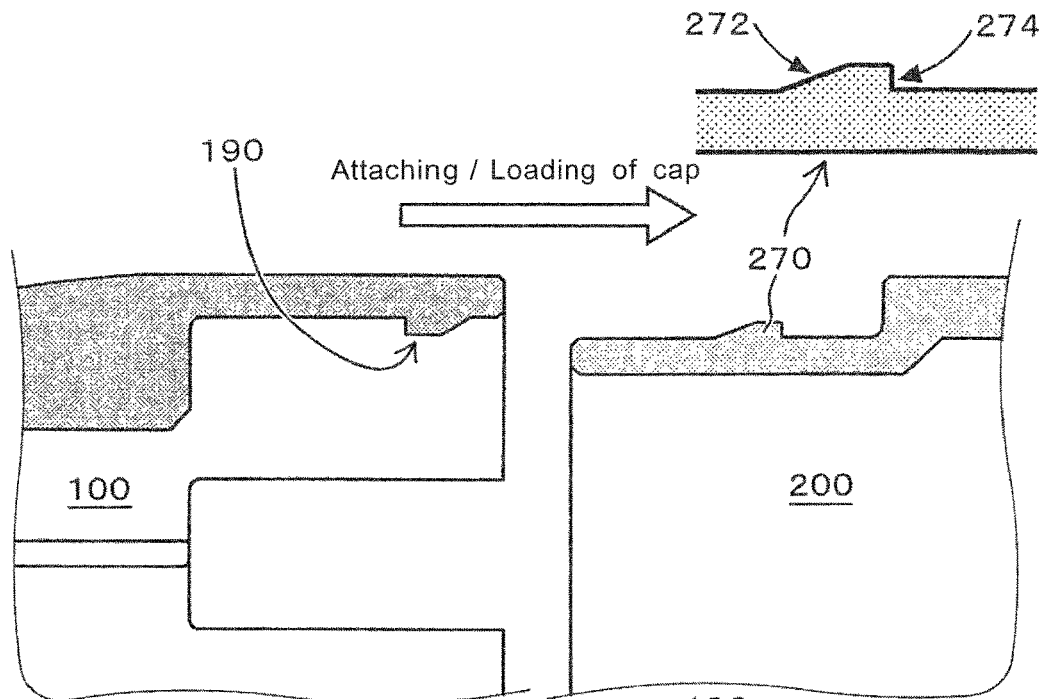
FIGS. 8A to 8C are schematic cross-sectional views for explaining a snap fitting at the time of a cap attachment.
Figure 8B:
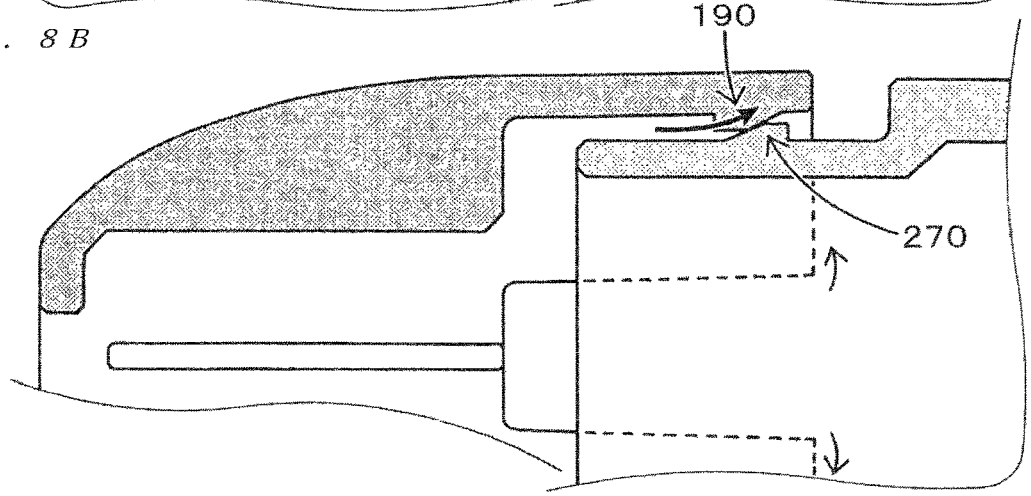
Figure 8C:
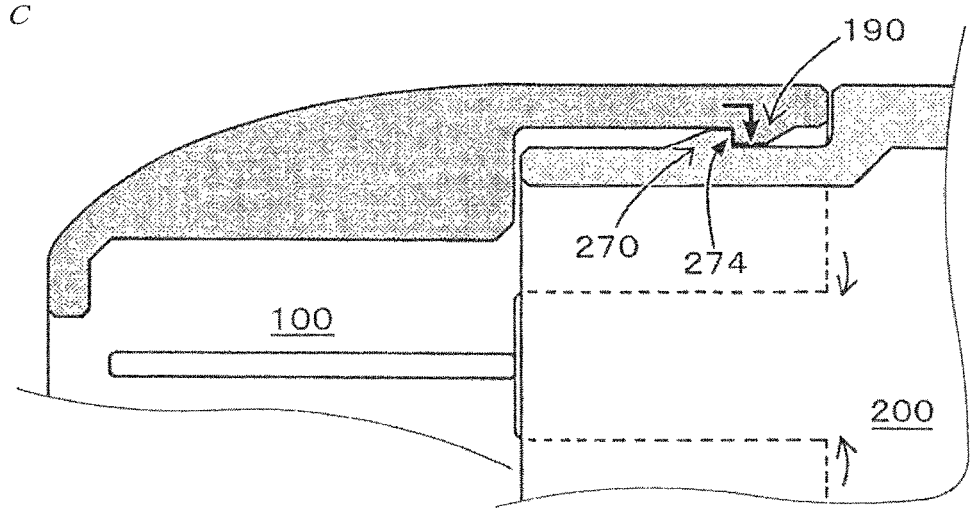

When the injector cap is attached to the injector housing, it is preferred that the first raised portion of the injector cap is capable of sliding on the groove region of the injector housing, followed by a riding of the first raised portion over the second raised portion. In other words, the first raised portion preferably rides over the second raised portion, while the first raised portion being sliding on the groove region at the time when the injector cap is attached. More specifically, the first raised portion 190 moves while being sliding on the groove region 260 such that the first raised portion is guided by the paired banks 250 of the injector housing 200, during which time the first raised portion 190 preferably rides over the second raised portion 270 (see also the changes in the injector over time as shown in FIGS. 8A to 8C). This means that the first raised portion 190, which slides along the groove region 260 inside the banks 250, rides over the second raised portion 270 while keeping its position along the groove region 260.

According to a preferred embodiment of the present invention, a snap fitting is provided through the riding of the first raised portion 190 moving along the groove region 260 over the second raised portion 270. The snap fitting of the first raised portion 190 can preferably complete the attaching of the injector cap to the injector housing. It is preferred that the second raised portion 270 has a taper surface (which gradually increases a degree of its rise from the front side of the housing toward the rear side thereof), in which case the riding of the first raised portion 190 over the taper surface results in the snap fitting.

It is also preferred that the second raised portion 270 has a steep surface in addition to the taper surface. As shown in FIGS. 8A to 8C, an upper face of the second raised portion 270 is preferably composed at least of the taper surface 272 at a forward side thereof and a steep surface 274 at a rear side thereof. In this case, the snap fitting is caused by the riding of the first raised portion 190 located in the groove region 260 (i.e., located between the paired banks 250) over the taper surface 272 of the second raised portion 270, followed by positioning of the first raised portion 190 at the rear of the steep surface 274 of the second raised portion 270. Through such snap fitting, the attaching of the injector cap to the injector housing is performed. As such, when the injector cap is in attachment to the injector housing, the first raised portion is positioned inside the pair of banks and at a rear of the steep surface of the second raised portion. The positioning of the first raised portion at the rear of the steep surface of the second raised portion enables the first raised portion and the steep surface to be engaged with each other (more specifically, it enables the forward movement of the first raised portion to be inhibited by the steep surface of the second raised portion), and thereby providing a stability on the injector cap at a point in time after the attaching thereof. Similarly, the first raised portion 190 may also have a taper surface and/or a steep surface as its upper face. Specifically, the upper face of the first raised portion 190 is preferably composed at least of the steep surface at a forward side thereof and a taper surface at a rear side thereof.

At a point in time after the snap fitting, i.e., after the completed attaching of the injector cap, an incidental or unintentional detachment of the injector cap can be avoided. Specifically, an applying of a force for separating the injector cap 100 and the injector housing 200 away from each other causes the first raised portion 190 to be engaged by the steep surface 274 of the second raised portion 270, and thereby preventing the injector cap 100 from being detached from the injector housing 200 (see FIG. 8C). In other words, the relatively forward movement of the injector cap 100 with respect to the injector housing 200 is inhibited by the engagement of the first raised portion 190 with the steep surface 274 of the second raised portion 270. Because of "steep surface" in particular, the injector cap cannot be detached from the injector housing, even if the cap is strongly pulled in its non-slant orientation/straightforwardly along the axis direction of the injector. The phrase "steep surface" as used herein means that the surface in the cross-sectional view as shown in FIGS. 8A to 8C has an angle of 90°±20°, preferably 90°±10°, more preferably 90°±5° with respect to the axis direction of the injector.

In the present invention with the cap feature as described above, the injector cap can be attached to the injector housing through the snap fitting wherein the cap is loaded "in its non-slant orientation"/"straightforwardly" along the axis direction of the injector. While on the other hand, once the cap is attached, it cannot be detached "in its non-slant state"/"straightforwardly" from the injector housing. This means that the intentionally-attached cap cannot be incidentally or unintentionally detached from the housing, and thereby making it possible to ensure a more suitable safety of the injector.

The injector of the present invention has a unique feature also in terms of the detachment of the injector cap. In this regard, the first raised portion of the injector cap and the bank of the injector housing cooperate with each other upon the detaching of the cap.

Figure 9A:
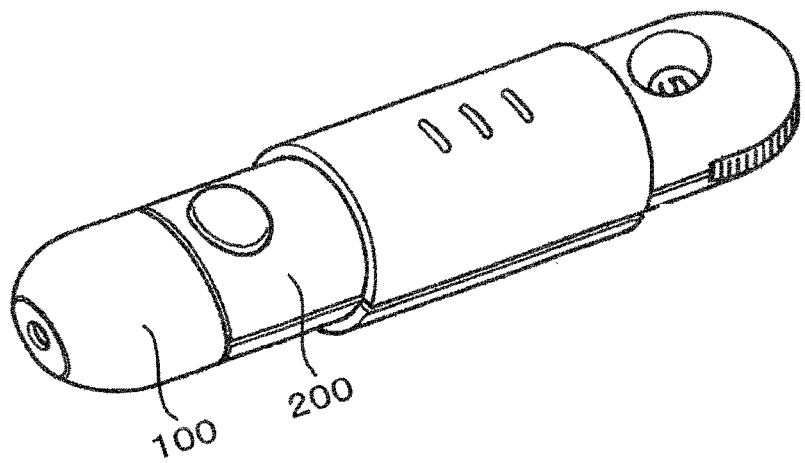
FIGS. 9A to 9C are schematic perspective views illustrating an embodiment of the injector wherein the injector cap is twist-rotated to be detached from the injector housing.
Figure 9B:
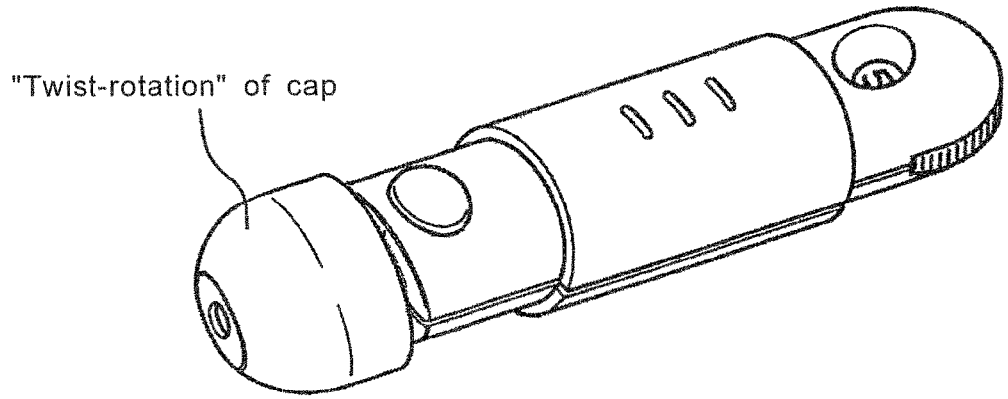
Figure 10A:
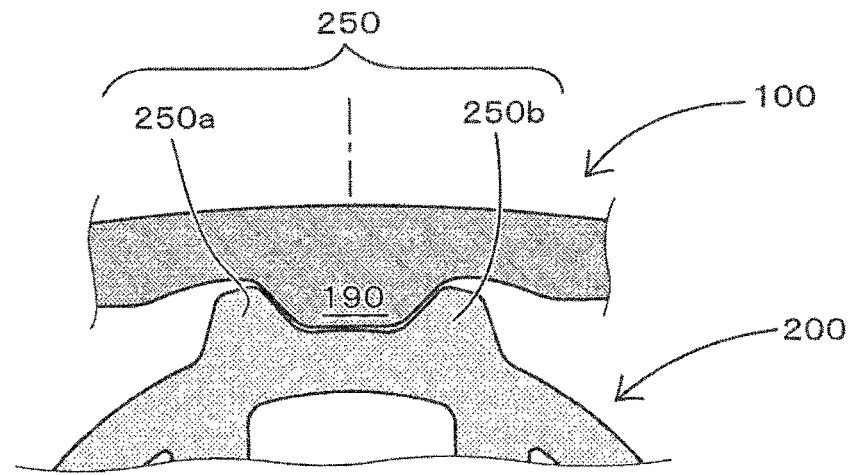
FIGS. 10A to 10O are schematic cross-sectional views for explaining a first raised portion riding over a bank upon the twist-rotating of the cap.
Figure 10B:
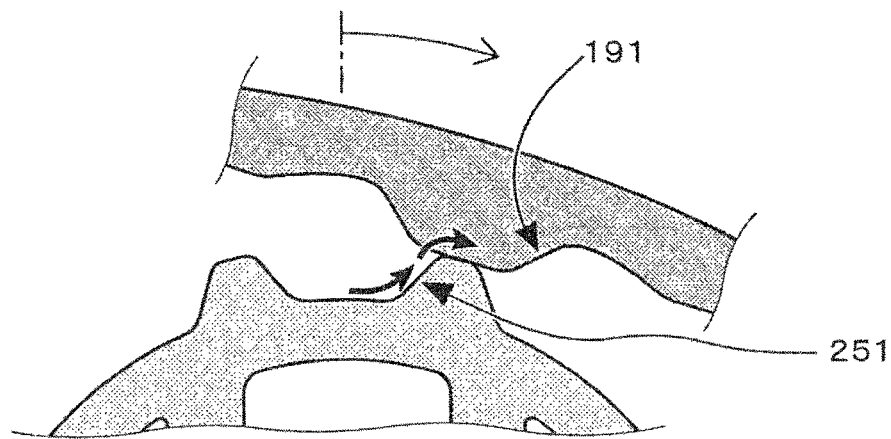
Figure 10C:
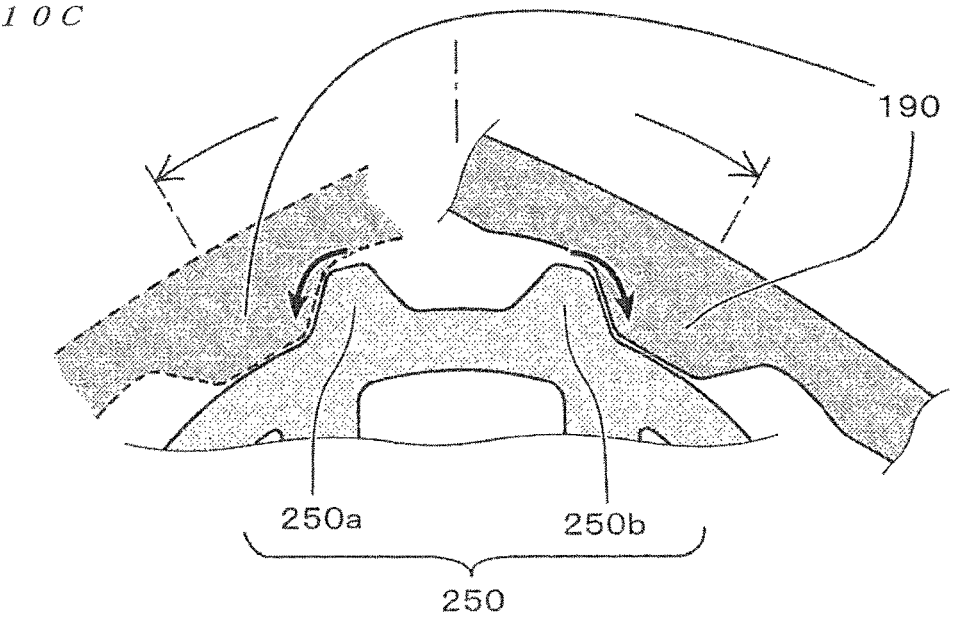
Figure 11:
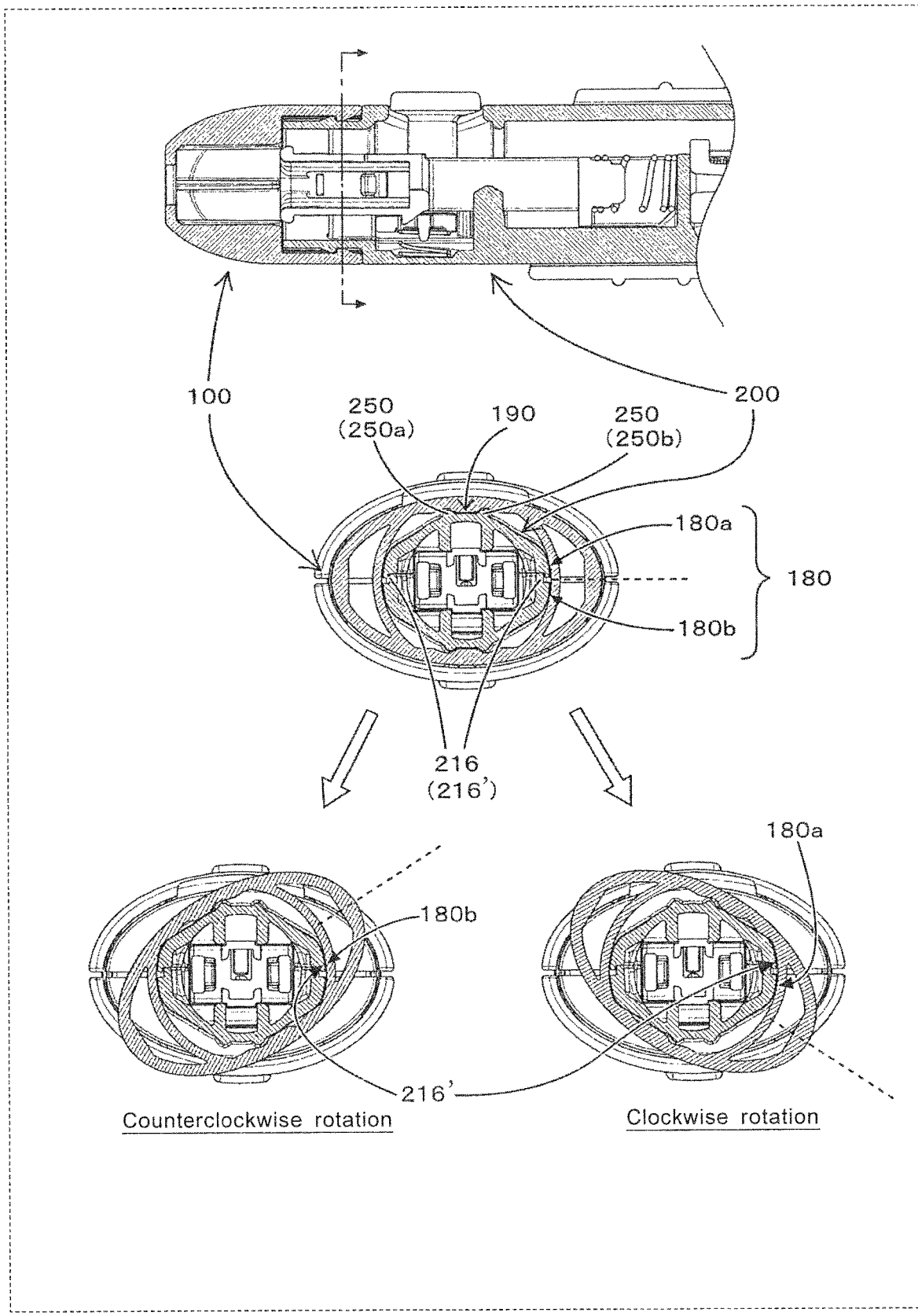
FIG. 11 includes schematic cross-sectional views for explaining an embodiment of the injector at the time when the injector cap is twist-rotated.

When the injector cap 100 in attachment to the injector housing 200 is rotated about the axis of the injector (i.e., when the cap is twisted as shown in FIGS. 9A and 9B), the first raised portion 190 of the injector cap 100 can ride over one of the paired banks 250 of the injector housing 200 (see FIGS. 10A to 10C and also see FIG. 11). As shown in FIGS. 10A to 10C, the first raised portion 190 in a fit-in engagement with the paired banks 250 is forced to move out of the interior of the banks 250, and thereby the fit-in engagement of the first raised portion 190 is released. More specifically, a side face 191 of the first raised portion 190 rides over an internal side 251 of one of the paired banks 250 while being sliding on such internal side 251, and thereby the fit-in engagement between the first raised portion 190 and the banks 250 is released (see FIGS. 10B and 10C in particular). As can be seen from FIGS. 10A to 10C, both of the side face 191 of the first raised portion 190 and the internal side 251 of one of the paired banks 250 respectively may have a form of non-steep surface, in which case the cross-sectional shapes of them may be preferably complementary to each other.

Figure 9C:
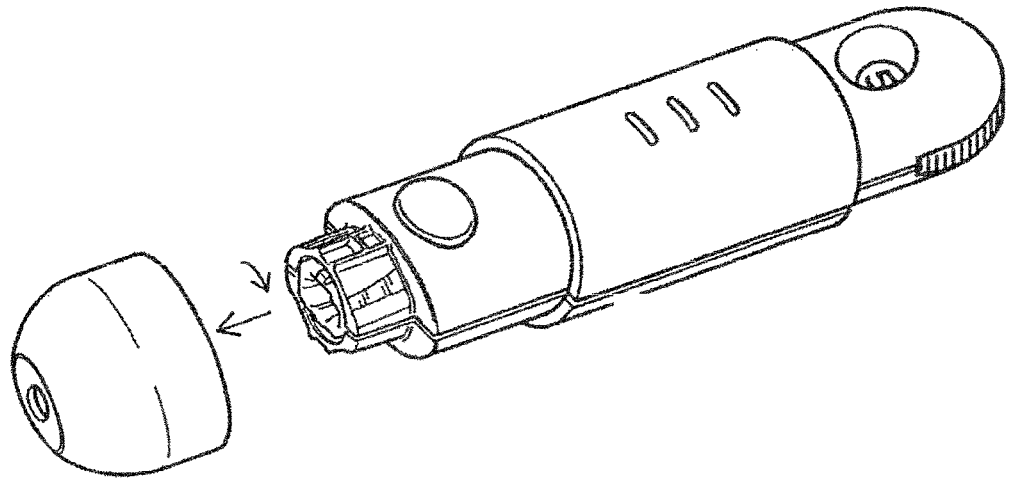

The riding of the first raised portion over the one of the paired banks (the riding being due to the rotation of the injector cap with respect to the injector housing) no longer causes the first raised portion to be engaged with respect to the steep surface, and thereby enabling the injector cap to be detached from the injector housing. See FIGS. 9B and 9C. The pulling of the injector cap "straightforwardly" in the axis direction of the injector with no twisting of the cap causes the first raised portion 190 to be engaged by the steep surface 274 of the second raised portion 270, which results in a prevention of the detachment of the injector cap. While on the other hand, when the injector cap is twisted/rotated with respect to the injector housing, then the engagement between the first raised portion 190 and the steep surface 274 is released, and thereby enabling the injector cap to be detached from the injector housing.

The injector of the present invention has an improved convenience on the rotation of the cap in the detaching thereof. Specifically, as shown in FIG. 10O and FIG. 11, the injector cap 100 has a reversible direction of the rotation with respect to the injector housing. More specifically, the injector cap 100 can be rotated in a clockwise direction with respect to the injector housing, and also the injector cap 100 can be rotated in a counterclockwise direction with respect to the injector housing. Either one of the clockwise and counterclockwise rotations enables the first raised portion to ride over the bank, and thereby avoiding the engagement of the first raised portion with respect to the steep surface of the second raised portion. The detaching of the injector cap is associated with the pair of banks 250, especially one bank 250a of the pair or the other bank 250b of the pair. For example, as shown in FIG. 10O, when the injector cap 100 is rotated clockwise with respect to the injector housing 200, the first raised portion 190 rides over one of the paired banks, e.g., the bank 250b, and thereby releasing the engagement of the first raised portion 190 with respect to the steep surface 274 of the second raised portion (see FIGS. 8A-8C). While on the other hand, when the injector cap 100 is rotated counterclockwise with respect to the injector housing 200, the first raised portion 190 rides over the other of the paired banks, e.g., the bank 250a, and thereby releasing the engagement of the first raised portion 190 with respect to the steep surface 274 of the second raised portion (see FIGS. 8A-8C).

According to the injector of the present invention, the more improved convenience on the rotating/twisting of the cap for the purpose of detaching thereof is provided for user. The rotation of the injector cap for the detachment of the cap is not unlimited. The rotation of the injector cap is limited within the predetermined range, and thereby making it possible for user to more easily understand a completion of the releasing of the engagement between the first raised portion 190 and the steep surface 274 of the second raised portion. More specifically, as shown in the middle and lower of FIG. 11, the inner surface of the injector cap 100 and the outer surface of the injector housing 200 are capable of making a local contact with each other, and thereby the rotation of the injector cap with respect to the injector housing is limited within the predetermined range. By way of example, the rotation of the injector cap about the injector axis with respect to the injector housing is limited within about ±30°.

The slant orientation of the injector cap through the above rotation (i.e., twisting/twist-rotation of the cap) makes it possible to release the engagement between the first raised portion and the steep surface, which leads to the detachment of the injector cap from the injector housing. The same holds true for the attachment of the injector cap. The once-detached injector cap 100 can be smoothly attached to the injector housing 200 without no substantial resistance when being kept in its slant orientation.

Figure 12:
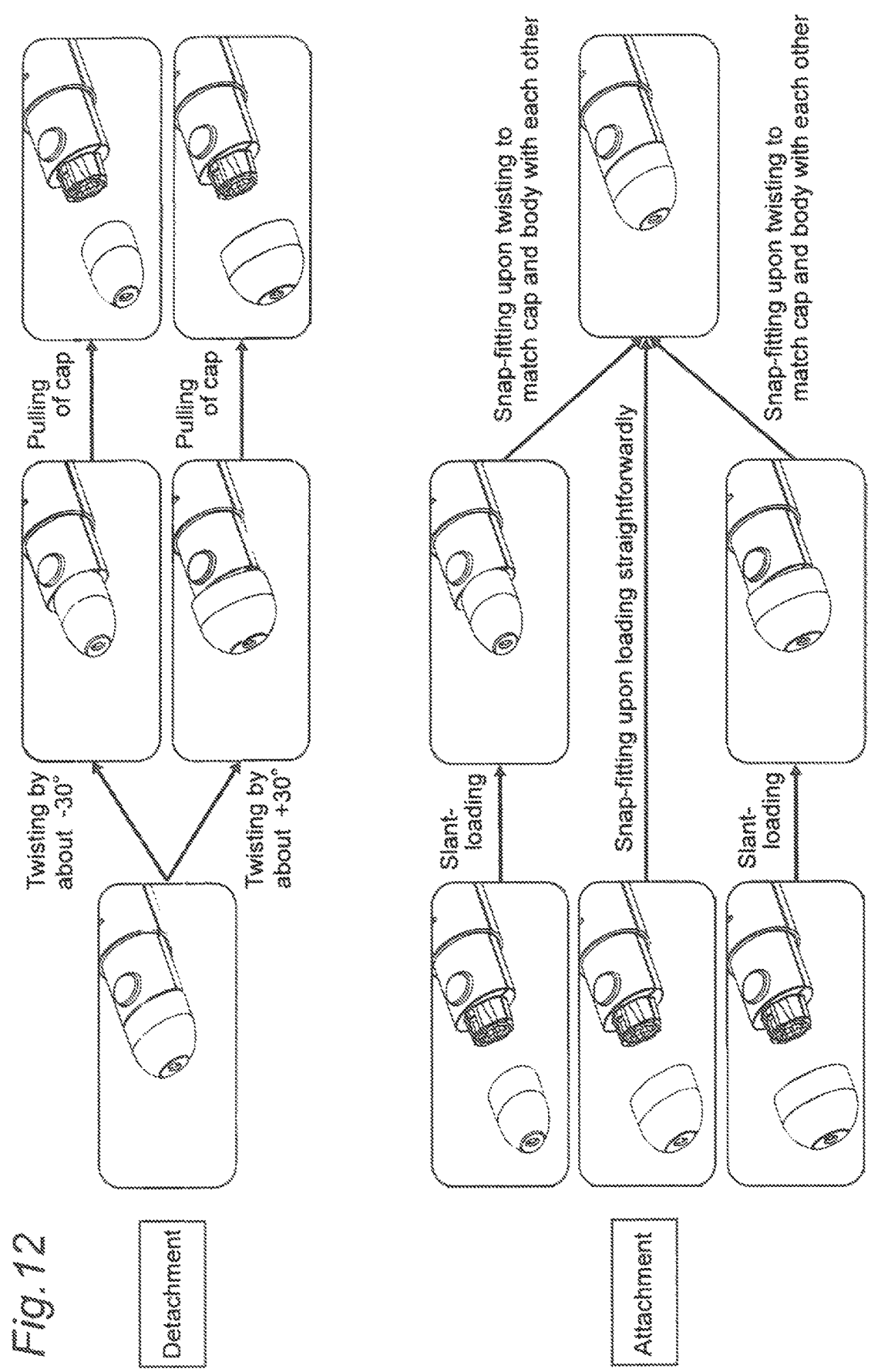
FIG. 12 includes schematic perspective views collectively illustrating the attaching and detaching of the injector cap regarding the injector according to the present invention.

The cap attaching and detaching regarding the injector according to the present invention are illustrated in collective manner in FIG. 12. As shown in FIG. 12, when the injector cap is twist-rotated clockwise by about 30° for example, then the cap can be relatively easily detached from the injector housing. Similarly, when the injector cap is twist-rotated counterclockwise by about 30°, the cap can be also relatively easily detached from the injector housing. When the once-detached cap is loaded straightforwardly/in its non-slant state with respect to the front end portion of the injector housing, then the injector cap can be relatively easily attached to the housing through the snap fitting. While on the other hand, the injector cap in attachment to the injector housing cannot be detached straightforwardly/in its non-slant state. Moreover, when the once-detached cap is loaded to the injector housing while being kept in its slant orientation to have the clockwise twist-rotation of about 30°, then the cap is smoothly matched with respect to the housing with no substantial friction resistance. After that, when the injector cap is twist-rotated counterclockwise such that the non-slant orientation of the cap is provided, then the cap is snap-fitted to the housing, resulting in the completion of the attaching of the injector cap. Similarly, when the once-detached cap is loaded to the injector housing while being kept in its slant orientation to have the counterclockwise twist-rotation of about 30°, then the cap is smoothly matched with respect to the housing with no substantial friction resistance. After that, when the injector cap is twist-rotated clockwise such that the non-slant orientation of the cap is provided, then the cap is snap-fitted to the housing, resulting in the completion of the attaching of the injector cap. As such, the injector of the present invention particularly has the improved convenience in terms of the attaching and detaching of the injector cap.

The injector with at least one of the above characterizing features can be embodied in various forms. For example, the following embodiments can be possible.

(Neck Form of Front End Portion of Housing)

The front end portion of the injector housing may have suitable form for the attaching and detaching of the injector cap. As shown in FIG. 7, the injector housing 200 may be provided with a neck portion 215 configured to have a reduced dimension of the front end portion 210 of the housing. This means that the front end portion 210 of the injector housing has a smaller size than that of the main body of the injector housing in the transverse direction of the injector. It is preferred that, when the attaching of the injector cap is performed, the cap is assembled with the injector housing such that the front end portion of the injector housing, i.e., the neck portion is covered with the injector cap. The term "neck portion" as used herein means an open-end portion of the housing, the open-end portion being smaller than that of the main body of the housing to provide "neck-like form" in the housing as a whole.

In the case where the injector housing 200 has the neck form at the front end portion thereof, it is preferred that the paired banks 250 are located on an outer face 215A of the neck portion 215 of the housing. In this case, it is also preferred that the groove region 260 positioned inside the paired banks has the second raised portion 270 on the outer face 215A of the neck portion 215 of the housing. When the attaching of the injector cap 100 is performed such that the neck portion 215 is covered with the cap 100, the first raised portion 190 fits into the paired banks 250 of the neck portion 215, and subsequently the first raised portion 190 of the cap rides over the second raised portion 270 of the housing while being sliding in the groove region 260. The riding of the first raised portion 190 over the second raised portion 270 consequently leads to the snap-fitting, which completes the attaching of the injector cap to the injector housing.

(Curved Wall of Injector Cap)

In particular, the internal structure of the injector cap may have a suitable form for attaching and detaching the cap. As shown in FIG. 4, it is preferred that the injector cap 100 further comprises a curved wall 180 inside an outer wall 130 of the cap, for example. The curved wall 180 is located inside the outer wall 130 of the cap in the transverse direction of the injector. The curved wall 180 may be provided as a pair of curved walls. As can be seen from FIG. 4, the curved wall 180 may have a modified/smaller form with respect to a part of the outer wall 130 (i.e., with respect to a side portion of the outer wall 130). The curved walls 180 in the cross-sectional view may extend as a whole along the short axis of the approximately the elliptical shape of the injector cap.

It is preferred in the case of the curved wall that, when the injector cap is in attachment to the injector housing, the neck portion 215 of the injector housing 200 is positioned inside the curved wall 180 of the injector cap 100. This enables the curved wall 180 to be suitably guided by the neck portion 215 upon the attaching and detaching of the injector cap. As a result, the smoother attachment and detachment of the injector cap with respect to the injector housing can be facilitated. In particular, the backlash and play upon the attaching and detaching of the injector cap can be effectively reduced, and thereby providing a smoother operability with user. For example, when the injector cap is twist-rotated, the curved wall slides on the neck portion of the injector housing, which leads to an effective reduction in the backlash and play felt by the user. The inner surface of the curved wall and the outer periphery surface of the neck portion are capable of sliding on each other upon the rotation of the injector cap (see FIG. 11 in particular). In the case where the cap is twist-rotated in clockwise manner (see right-lower in FIG. 11), the inner surface in one 180a of halved portions of the curved wall 180 and the outer periphery surface 216' in lateral part 216 of the neck portion 215 are capable of sliding on each other. While on the other hand, in another case where the cap is twist-rotated in counterclockwise manner (see left-lower in FIG. 11), the inner surface in the other 180*b* of halved portions of the curved wall 180 and the outer periphery surface 216' in lateral part 216 of the neck portion 215 are capable of sliding on each other.

Figure 13:
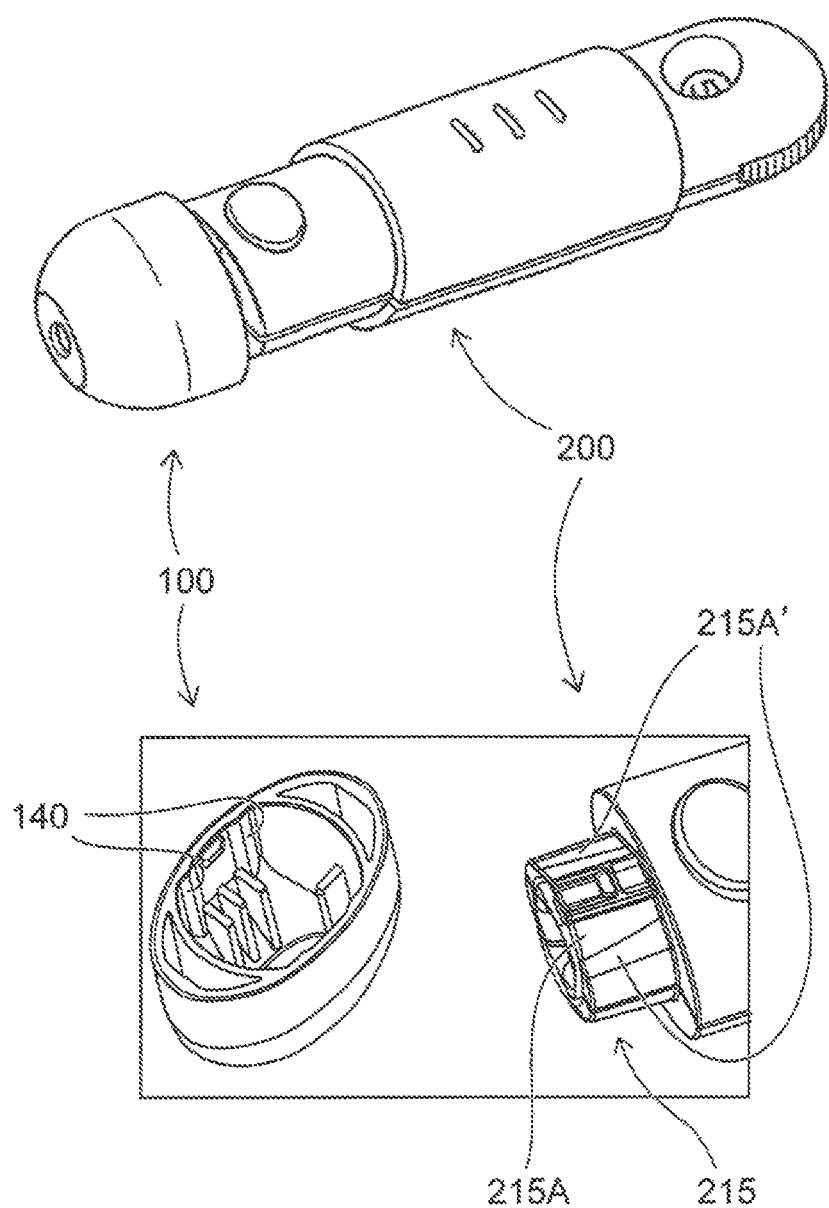
FIG. 13 includes schematic perspective views for explaining parts/portions associated with a limitation on the rotation of the injector cap, the limitation being within the predetermined range/degree of the cap rotation.

As described above, the rotation of the injector cap with respect to the injector housing is preferably limited within the predetermined range, which can be caused by a local contact between the inner surface of the injector cap and the outer surface of the injector housing. More specifically, the limitation on the rotation of the injector cap is preferably due to the mutual contact between "ridge 140 provided in the inner surface of the injector cap 100" and "local region of the outer surface 215A of the neck portion 215 (especially, local outer surface 215A' positioned adjacent to the above lateral part)", as shown in FIG. 13.

(Elastic Deformation)

The injector of the present invention may be elastically deformable to more suitably perform the attaching and detaching of the cap. For example, at least one of the injector cap and the injector housing is elastically deformable, and thereby the attaching and detaching of the injector cap is suitably facilitated.

For example, when the injector cap is loaded to the front end of the injector housing straightforwardly/in its non-slant orientation so that the snap fitting as described above is performed, it is preferred that at least one of the injector cap and the neck portion of the injector housing is elastically deformed. This makes it possible for the first raised portion 190 sliding on the groove 260 to more smoothly ride over the second raised portion 270, and thereby giving a more suitable snap fitting. That is, more natural snap-fitting is given for the attaching of the cap. Moreover, when the injector cap in attachment to the injector housing is twist-rotated for the detachment of the cap, it is also preferred that at least one of the injector cap and the neck portion of the injector housing is elastically deformed. This also makes it possible for the first raised portion 190 between the paired banks to more smoothly ride over the bank 250, and thereby the snap-fit feeling is given more naturally.

The elastic deformity may be due to the structure of the injector. Alternatively, the elastic deformity may be due to the material of the injector. By way of example, the injector cap may be provided with a partial cutout, and thereby providing the elastic deformation of the injector in terms of the cap structure. In this regard, the curved wall 180 of the injector cap 100 may have the partial cutout 185 (see FIG. 4) such that the injector cap 100 is elastically deformable. When the injector cap is loaded to the front end portion of the injector housing straightforwardly/in its non-slant orientation to perform the snap fitting, the injector cap is elastically deformed due to the partial cutout 185, and thereby resulting in the more suitable snap fitting. Alternatively, when the injector cap in attachment to the injector housing is twist-rotated for the detachment of the cap, the injector cap is also elastically deformed due to the partial cutout 185 of the cap, which can bring about the more suitable snap feeling for user.

Figure 14:
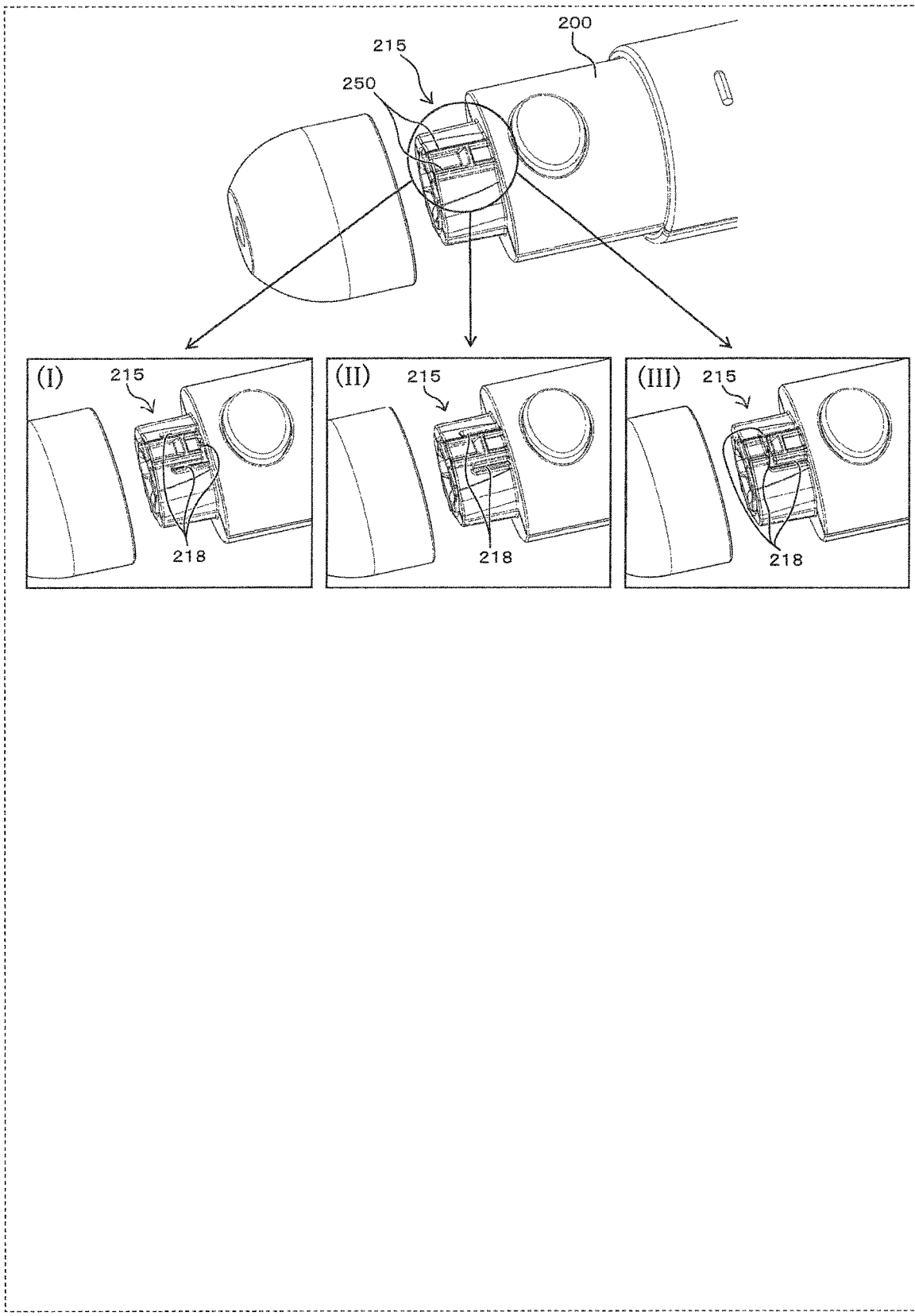
FIG. 14 includes schematic perspective views for explaining an elastic deformation of the injector housing.

Similar to the injector cap, the injector housing may also be provided with a partial cutout, and thereby providing the elastic deformation of the injector in terms of the housing structure. In this regard, the neck portion 215 of the injector housing 200 may have the partial cutout 218 (see FIG. 14) such that the neck portion 215 is elastically deformable. The partial cutout 218 preferably has such a form that it penetrates through the wall of the neck portion. When the injector cap 100 is loaded to the neck portion 215 straightforwardly/in its non-slant orientation to perform the snap fitting, the injector housing (the neck portion 215 thereof in particular) is elastically deformed due to the partial cutout 218, and thereby resulting in the more suitable snap fitting. Alternatively, when the injector cap in attachment to the injector housing is twist-rotated for the detachment of the cap, the injector housing (the neck portion 215 thereof in particular) is also elastically deformed due to the partial cutout 218, which can bring about the more suitable snap feeling for user. It is preferred that the partial cutout 218 of the neck portion 215 has a form of slot extending in the pricking direction (see FIG. 14). This makes it possible for the neck portion 215 to more suitably elastically deformed. The partial cutout 218 in the form of slot extending in the pricking direction, which is provided on the outer surface of the neck portion, may be located outside the paired banks 250. In particular, the partial cutout 218 may be positioned adjacent to each of the banks 250 as shown in FIG. 14 for example. Alternatively, the slot-like partial cutout 218 may extend not only in the pricking direction, but also in the direction orthogonal to the pricking direction. For example, as shown in (I) and (III) of FIG. 14, the plan view of the partial cutout 218 may have "U-shaped with all corners in substantially straight angles", and thereby the elastic deformation of the injector cap can be more suitably promoted.

The partial cutout for the elastic deformation may be provided in any one of the injector cap and the neck portion of the injector housing. Of course, the partial cutout can be provided in both of the injector cap and the neck portion of the injector housing, in which case the elastic deformation can be more easily achieved.

Although some embodiments of the present invention have been hereinbefore described, such embodiments are only for illustrative purpose as typical examples, and thus the present invention is not limited to these embodiments. It will be readily appreciated by those skilled in the art that various modifications are possible without departing from the scope of the invention. For example, the pricking needle 410 has a "needle form" whose uppermost is wholly sharpened, but the present invention is not necessarily limited thereto. The pricking needle 410 may have a "blade form" having a sharpened one-side face at its tip portion, for example.

It should be noted that the present invention as described above includes the following aspects:

The First Aspect:

An injector for launching a lancet to provide a pricking, the injector comprising:

a plunger capable of launching the lancet in a pricking direction, the lancet being in attachment to the plunger;

an injector housing which surrounds the plunger; and an injector cap capable of being attached and detached with respect to the injector housing, wherein an inner face of the injector cap is provided with a rib, and wherein the rib of the injector cap and the plunger are capable of contacting with each other, the plunger being moving for the launching of the lancet.

The Second Aspect:

The injector according to the first aspect, wherein the rib is provided as a pair of ribs.

The Third Aspect:

The injector according to the second aspect, wherein the two pairs of ribs are provided wherein an opposing direction of the ribs in one of the two pairs is orthogonal to another opposing direction of the ribs in the other of the two pairs.

The Fourth Aspect:

The injector according to any one of the first to third aspects, wherein the rib is provided as plural ones, and wherein the plurality of ribs are symmetrical to each other in a cross-sectional view of the injector cap, the view being taken along a direction orthogonal to the pricking direction.

The Fifth Aspect:

The injector according to any one of the first to fourth aspects, wherein the injector cap has approximately an elliptical shape in a cross-sectional view of the cap, the view being taken along a direction orthogonal to the pricking direction.

The Sixth Aspect:

An injector for launching a lancet to provide a pricking, the injector comprising:

a plunger capable of launching the lancet in a pricking direction, the lancet being in attachment to the plunger;

an injector housing which surrounds the plunger; and an injector cap capable of being attached and detached with respect to the injector housing, wherein the injector cap has a first raised portion at an inner face of the cap, and wherein the injector housing has a pair of banks in an outer face of the housing, and also a second raised portion at a groove region provided inside the banks.

The Seventh Aspect:

The injector according to the sixth aspect, wherein each of the banks extends along the pricking direction.

The Eighth Aspect:

The injector according to the sixth or seventh aspect, wherein the first raised portion is capable of fitting to the groove region.

The Ninth Aspect:

The injector according to any one of the sixth to eighth aspects, wherein, when the injector cap is attached to the injector housing, the first raised portion is capable of sliding on the groove region, followed by a riding of the first raised portion over the second raised portion.

The Tenth Aspect:

The injector according to any one of the sixth to ninth aspects, wherein an upper face of the second raised portion is composed at least of a taper surface at a forward side thereof and a steep surface at a rear side thereof.

The Eleventh Aspect:

The injector according to the tenth aspect, wherein, when the injector cap is in attachment to the injector housing, the first raised portion is positioned inside the pair of banks and at a rear of the steep surface of the second raised portion.

The Twelfth Aspect:

The injector according to the eleventh aspect, wherein an applying of a force for separating the injector cap and the injector housing away from each other causes the first raised portion to be engaged by the steep surface, and thereby preventing the injector cap from being detached from the injector housing.

The Thirteenth Aspect:

The injector according to any one of the sixth to twelfth aspects, wherein, when the injector cap in attachment to the injector housing is rotated about an axis of the injector with respect to the injector housing, the first raised portion of the injector cap is capable of riding over one of the banks of the injector housing.

The Fourteenth Aspect:

The injector according to the thirteenth aspect when appendant to the twelfth aspect, wherein the riding of the first raised portion over the one of the banks no longer causes the first raised portion to be engaged with respect to the steep surface, and thereby enabling the injector cap to be detached from the injector housing.

The Fifteenth Aspect:

The injector according to the thirteenth or fourteenth aspect, wherein the inner surface of the injector cap and the outer surface of the injector housing are capable of making a local contact with each other, and thereby the rotation of the injector cap with respect to the injector housing is limited within a predetermined range.

The Sixteenth Aspect:

The injector according to any one of the thirteenth to fifteenth aspects, wherein the injector cap has a reversible direction of the rotation.

The Seventeenth Aspect:

The injector according to any one of sixth to sixteenth aspects, wherein the injector housing is provided with a neck portion configured to have a reduced dimension of a front end portion of the injector housing, and wherein the banks are located on an outer face of the neck portion.

The Eighteenth Aspect:

The injector according to the seventeenth aspect, wherein the injector cap further comprises a curved wall inside an outer wall of the cap, and wherein, when the injector cap is in attachment to the injector housing, the neck portion of the injector housing is positioned inside the curved wall.

The Nineteenth Aspect:

The injector according to the eighteenth aspect when appendant to the thirteenth aspect, wherein an inner face of the curved wall and the outer face of the neck portion are capable of sliding on each other when the injector cap is rotated.

The Twentieth Aspect:

The injector according to any one of the seventeenth to nineteenth aspects, wherein at least one of the injector cap and the injector housing is elastically deformable, and thereby facilitating the attaching and detaching of the injector cap.

The Twenty-First Aspect:

The injector according to the twentieth aspect when appendant to the seventeenth aspect, wherein the neck portion has a partial cutout, and thereby enabling the neck portion to be elastically deformed.

EXAMPLES

In order to confirm the effects of the improved needle linearity regarding the injector of the present invention, tests were conducted.

Two types of injectors were used in the tests. Specifically, Injector A as "Example" and Injector B as "Comparative example" were used.

Injector of Type "A" (Example):

Injector with rib provided in injector cap thereof, the rib being for purpose of an improved linearity of pricking needle.

Injector of Type "B" (Comparative Example):

Injector with no rib provided in injector cap thereof, the rib being for purpose of an improved linearity of pricking needle.

The results are shown in the following Table 1 as well as FIG. 15.

TABLE 1

Wobbling of Pricking Needle (as indicator of Linearlity)

| | Type of Injector | |
|---|---|---|
| | INJECTOR "A" (Example) | INJECTOR "B" (Comparative example) |
| Setting for exposed needle tip | Maximum Setting (Daial setting for controlling of exposed needle tip: 7) | |
| Shooting direction of high-speed camera | Side Face of Device (Direction in which side face of launch button can be seen) | |
| Run 1 | 0.19 | 0.35 |
| 2 | 0.13 | 0.39 |
| 3 | 0.22 | 0.47 |
| 4 | 0.18 | 0.52 |
| 5 | 0.29 | 0.40 |
| 6 | 0.14 | 0.53 |
| 7 | 0.12 | 0.37 |
| 8 | 0.18 | 0.49 |
| 9 | 0.16 | 0.38 |
| 10 | 0.17 | 0.42 |
| AVE | 0.178 | 0.432 |
| MAX | 0.29 | 0.53 |
| MIN | 0.12 | 0.35 |

Figure 15:
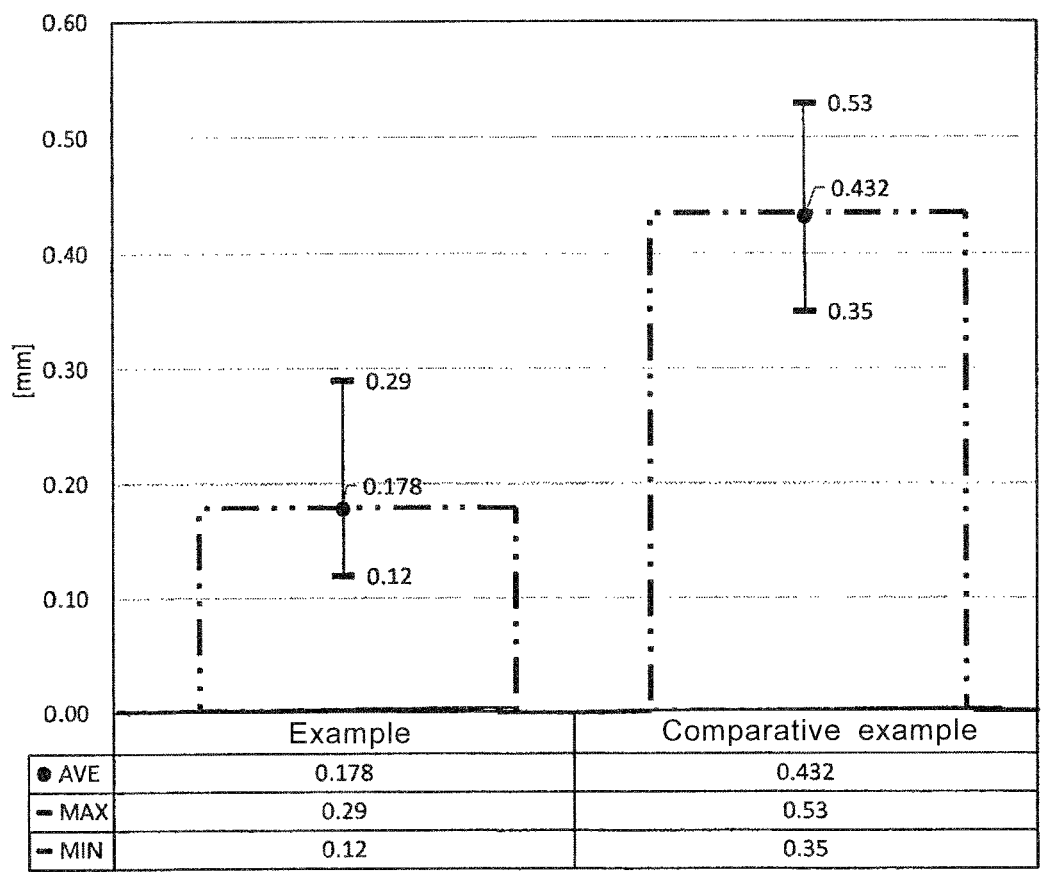
FIG. 15 shows the results for the confirmatory test of the effects of the improved linearity.
Figure 16:
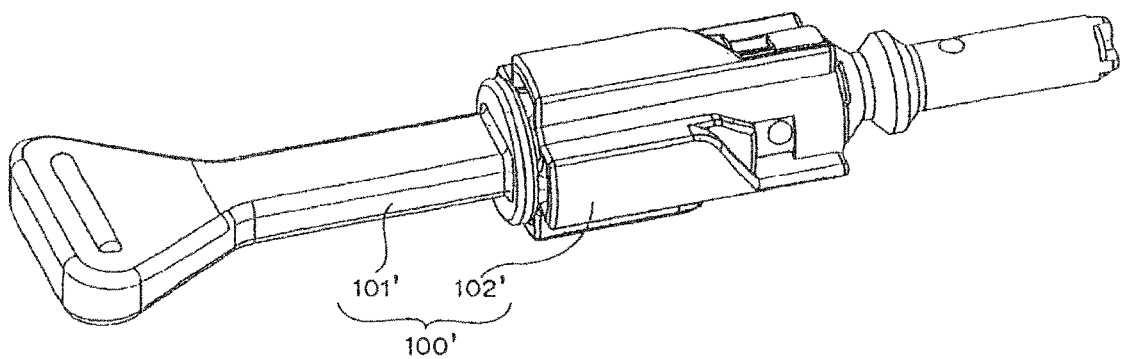
FIG. 16 is a perspective view showing an appearance of a lancet assembly (Prior Art).
Figure 17:
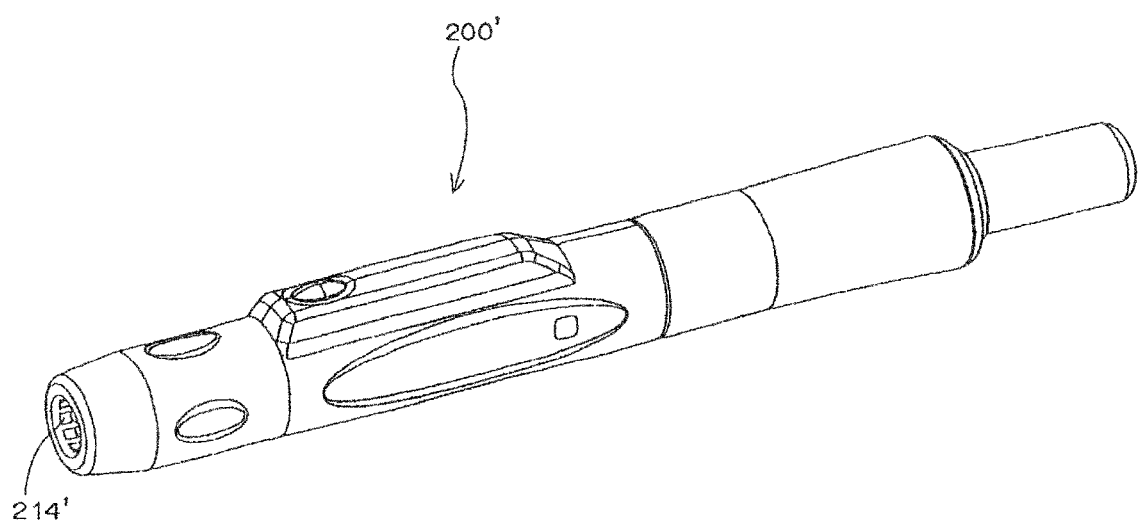
FIG. 17 is a perspective view showing an appearance of an injector (Prior Art).
Figure 18:
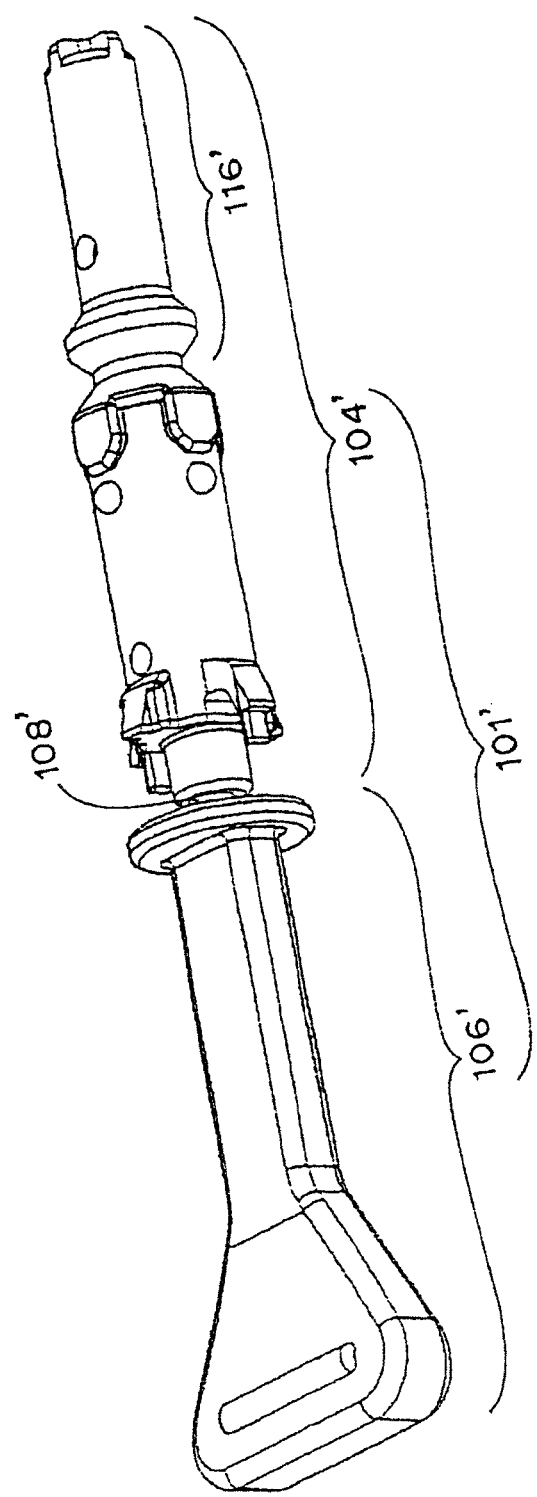
FIG. 18 is a perspective view showing an appearance of a lancet (Prior Art).
Figure 19:
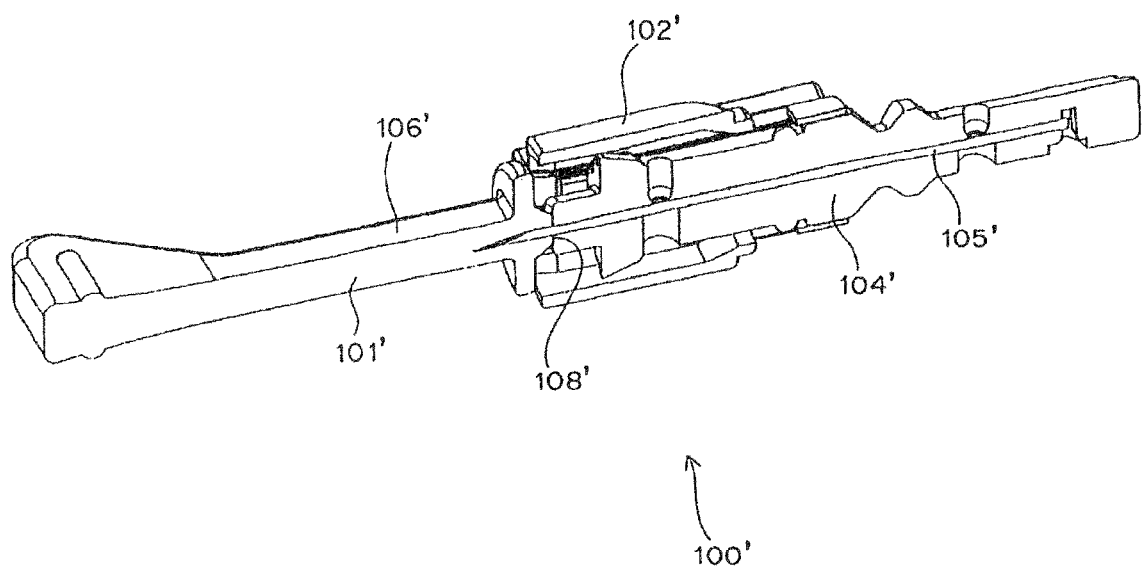
FIG. 19 is a perspective view showing the lancet of FIG. 18, cut away in half so as to make it easy to understand the inside of the lancet (Prior Art).
Figure 20:
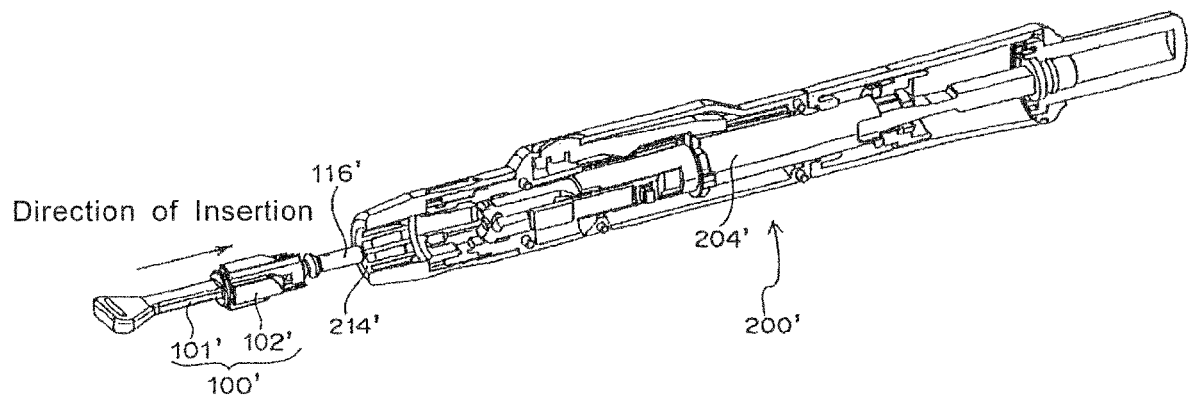
FIG. 20 is a perspective view showing the state before the lancet assembly is loaded into the injector (Prior Art).
Figure 21:
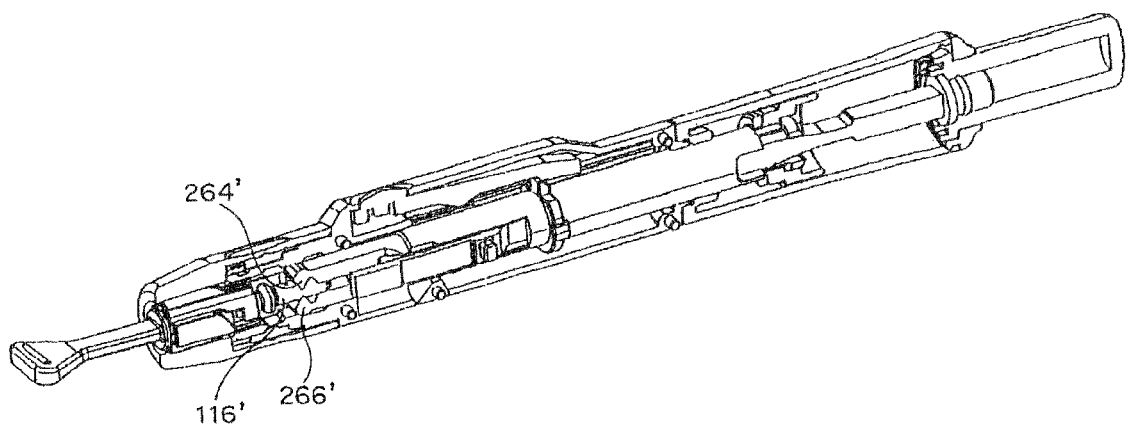
FIG. 21 is a perspective view showing the state in which the lancet is held by the tip of a plunger upon loading the lancet assembly (Prior Art).
Figure 22:
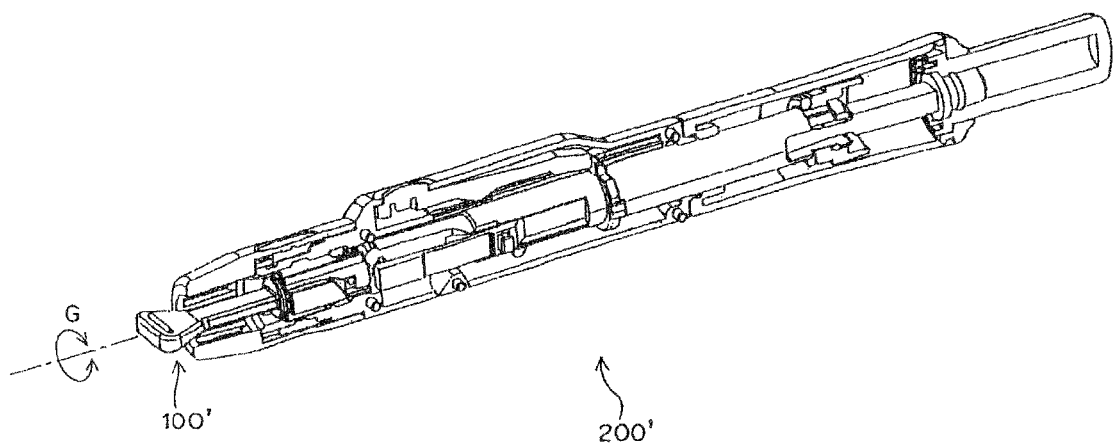
FIG. 22 is a perspective view showing the state of completion of loading the lancet assembly wherein the plunger cannot be retracted any longer (Prior Art).
Figure 23:
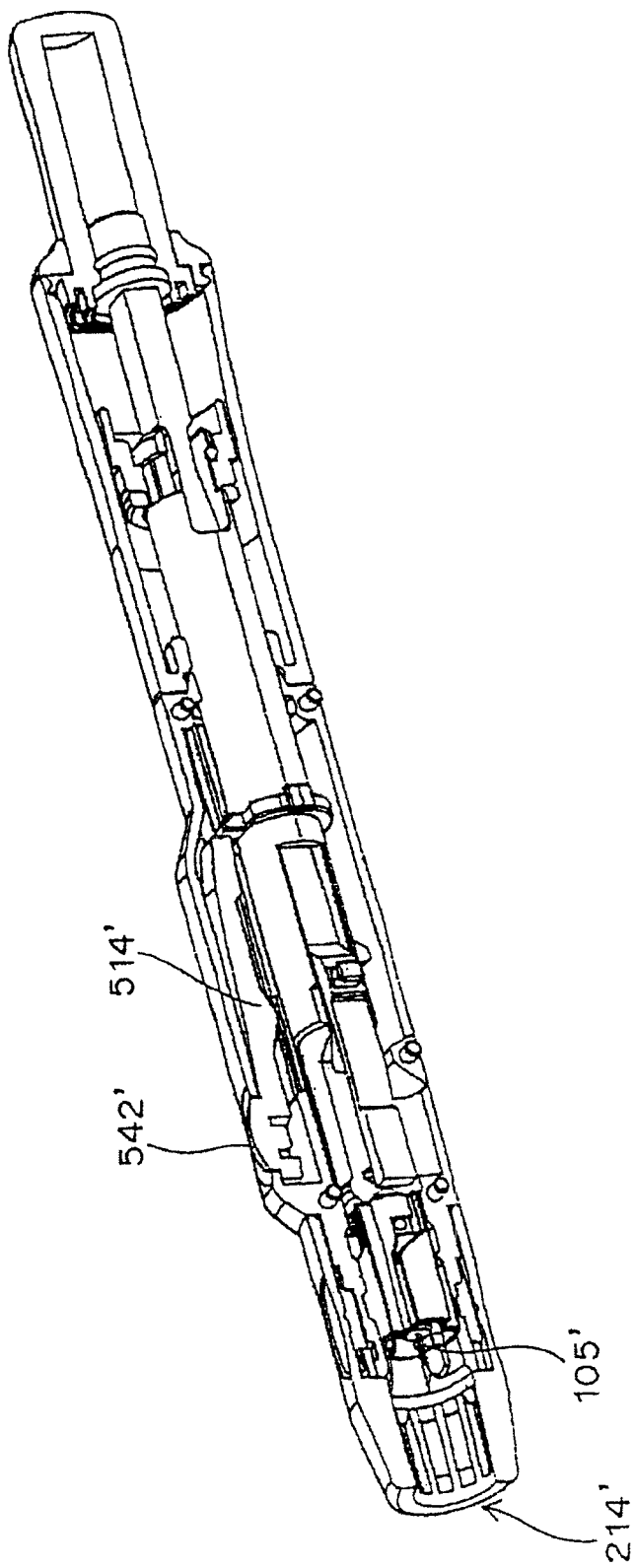
FIG. 23 is a perspective view showing the state in which a lancet cap has been removed and thus the lancet is ready for pricking (Prior Art).

As can be seen from the results of Table 1 and FIG. 15, the injector according to the present invention has an improvement in linearity of the pricking needle, i.e., in linear track/pathway of the pricking needle.

INDUSTRIAL APPLICABILITY

The injector according to the present invention is capable of launching the lancet for the purpose of serving to prick. Thus, the injector of the present invention can be used as a blood-sampling device in combination with the lancet.

CROSS REFERENCE TO RELATED PATENT APPLICATION

The present application claims the right of priority of Japanese Patent Application No. 2017-118871 (filed on Jun. 16, 2017, the title of the invention: "INJECTOR"), the disclosures of which are all incorporated herein by reference.

REFERENCE NUMERALS

100 . . . Injector cap, 110 . . . Rear end of injector cap, 115 . . . Rear edge of injector cap, 120 . . . Front end of injector (Tip portion of injector cap), 125 . . . Pricking opening, 130 . . . Outer wall of injector cap, 140 . . . Ridge of inner face of injector cap, 150 . . . Rib, 155 . . . Top edge/apex of rib, 160A . . . Inner face of injector cap, 160B . . . Inner face of injector cap, 170A . . . Inner face of injector cap, 170B . . . Inner face of injector cap, 180 . . . Curved wall, 180*a* . . . One of approximately halved parts of curved wall, 180*b* . . . The other of approximately halved parts of curved wall, 185 . . . Partial cutout, 190 . . . First raised portion, 191 . . . Side face of first raised portion, 200 . . . Injector housing, 210 . . . Forward portion/front end portion of injector housing, 215 . . . Neck portion of injector housing, 215A . . . Outer face of neck portion, 215A' . . . Local outer-face region, 216 . . . Side of neck portion, 216' . . . Outer surface of side of neck portion, 218 . . . Partial cutout of neck portion, 220 . . . Plunger, 221 . . . Front portion of plunger, 225 . . . Lancet holder, 226 . . . Outer face of lancet holder, 226' . . . Convex of lancet holder surface, 230 . . . Charge member, 240 . . . Launch button, 250 . . . Bank (Paired banks), 250*a* . . . One of paired banks, 250*b* . . . The other of paired banks, 251 . . . Inner face of bank portion, 260 . . . Groove region, 270 . . . Second raised portion, 272 . . . Forward taper surface of second raised portion, 274 . . . Rear steep surface of second raised portion, 400 . . . Lancet, 410 . . . Pricking needle, 500 . . . Injector.

The invention claimed is:

1. An injector for launching a lancet to provide a pricking, the injector comprising:
a plunger capable of launching the lancet in a pricking direction, the lancet being in attachment to the plunger, the plunger comprising a lancet holder;
an injector housing which surrounds the plunger; and
an injector cap capable of being attached and detached with respect to the injector housing,
wherein the injector cap comprises a front opening and an inner face, the inner face of the injector cap comprising a first pair of ribs and a second pair of ribs, each of the ribs of the first and second pairs of ribs respectively extending from the inner face to a top edge/apex as viewed in a cross-section of the injector cap taken along a direction orthogonal to the pricking direction, the first pair of ribs opposing one another along a first direction orthogonal to the pricking direction, the second pair of ribs opposing one another in a second direction orthogonal to the first direction and orthogonal to the pricking direction,
wherein the respective top edges/apexes of the first and second pairs of ribs extend along the pricking direction, and
wherein the first and second pairs of ribs of the injector cap and the plunger are capable of contacting with each other at a point in time after a launching of the plunger, such that an outer face of a front portion of the plunger makes contact with one or more of the respective top edges/apexes of the first and second pairs of ribs of the injector cap.

2. The injector according to claim 1,
wherein the ribs of the first pair of ribs are symmetrical to each other as viewed in the cross-section of the injector cap taken along the direction orthogonal to the pricking direction.

3. The injector according to claim 1, wherein each of the ribs of the first and second pairs of ribs includes a plurality of sides extending between the inner face and the top edge/apex and extending along the pricking direction, and the first and second pairs of ribs are configured such that the plunger is not capable of making contact with the plurality of sides of the ribs of the first and second pairs of ribs.

4. An injector for launching a lancet to provide a pricking, the injector comprising:
a plunger capable of launching the lancet in a pricking direction, the lancet being in attachment to the plunger;
an injector housing which surrounds the plunger; and
an injector cap capable of being attached and detached with respect to the injector housing, the injector cap having approximately an elliptical shape as viewed in a cross-section of the injector cap taken along a direction orthogonal to the pricking direction,
wherein the injector cap has a first raised portion at an inner face of the injector cap, wherein the injector housing has a pair of banks in an outer face of the housing, and also a second raised portion in a groove provided inside the pair of banks, wherein each bank of the pair of banks extends along the pricking direction such that the groove extends between a first end and a second end along the pricking direction, and the second raised portion is located in the groove between the first end and the second end, wherein when the injector cap is attached to the injector housing, the first raised portion of the injector cap is capable of sliding on the groove of the injector housing and thereafter riding over the second raised portion, wherein with the injector cap attached to the injector housing:

with rotation of the injector cap about an axis of the injector, the first raised portion of the injector cap is capable of riding over one bank of the pair of banks of the injector housing, and wherein a portion of the inner face of the injector cap and a portion of the outer face of the injector housing are capable of making contact with each other to thereby limit rotation of the injector cap with respect to the injector housing within a predetermined range.

5. The injector according to claim 4, wherein the first raised portion is capable of fitting to the groove.

6. The injector according to claim 4, wherein an upper face of the second raised portion is composed at least of a taper surface at a forward side thereof and a steep surface at a rear side thereof.

7. The injector according to claim 6, wherein, when the injector cap is in attachment to the injector housing, the first raised portion is positioned inside the pair of banks and at a rear of the steep surface of the second raised portion.

8. The injector according to claim 7, wherein an applying of a force for separating the injector cap and the injector housing away from each other causes the first raised portion to be engaged by the steep surface, and thereby preventing the injector cap from being detached from the injector housing.

9. The injector according to claim 8, wherein the riding of the first raised portion over the one bank of the pair of banks no longer causes the first raised portion to be engaged with respect to the steep surface, thereby enabling the injector cap to be detached from the injector housing.

10. The injector according to claim 4, wherein the injector cap has a reversible direction of the rotation.

11. The injector according to claim 4, wherein the injector housing is provided with a neck portion configured to have a reduced dimension of a front end portion of the injector housing, and wherein the pair of banks are located on an outer face of the neck portion.

12. The injector according to claim 11, wherein the injector cap further comprises a curved wall inside an outer wall of the injector cap, and wherein, when the injector cap is in attachment to the injector housing, the neck portion of the injector housing is positioned inside the curved wall.

13. The injector according to claim 11, wherein the injector cap further comprises a curved wall inside an outer wall of the injector cap, wherein, when the injector cap is in attachment to the injector housing, the neck portion of the injector housing is positioned inside the curved wall, and wherein an inner face of the curved wall and the outer face of the neck portion are capable of sliding on each other when the injector cap in attachment to the injector housing is rotated with respect to the injector housing.

14. The injector according to claim 11, wherein at least one of the injector cap and the injector housing is elastically deformable, and thereby facilitating the attaching and detaching of the injector cap.

15. The injector according to claim 11, wherein the neck portion has a partial cutout such that the neck portion is elastically deformable, and thereby facilitating the attaching and detaching of the injector cap.

16. The injector according to claim 4, wherein the second raised portion and the pair of banks have an integrated form with each other.

17. The injector according to claim 4, wherein the second raised portion is configured such that it allows for attachment of the injector cap to the injector housing by allowing riding of the first raised portion over the second raised portion upon sliding of the first raised portion of the injector cap in the groove provided inside the pair of banks; and the second raised portion is further configured such that it prevents detachment of the injector cap to the injector housing upon application of a force along the pricking direction by preventing riding of the first raised portion over the second raised portion.

* * * * *